(12) United States Patent
Chance

(10) Patent No.: US 7,983,741 B2
(45) Date of Patent: Jul. 19, 2011

(54) EXAMINATION AND IMAGING OF BRAIN COGNITIVE FUNCTIONS

(75) Inventor: Britton Chance, Marathon, FL (US)

(73) Assignee: Non-Invasive Technology Inc., Philadelphia, PA (US)

( * ) Notice: Subject to any disclaimer, the term of this patent is extended or adjusted under 35 U.S.C. 154(b) by 64 days.

(21) Appl. No.: 12/157,185

(22) Filed: Jun. 7, 2008

(65) Prior Publication Data
US 2009/0062660 A1 Mar. 5, 2009

Related U.S. Application Data

(63) Continuation of application No. 10/752,440, filed on Jan. 5, 2004, now Pat. No. 7,840,257, and a continuation of application No. 10/618,579, filed on Jul. 10, 2003, now abandoned.

(60) Provisional application No. 60/438,229, filed on Jan. 4, 2003, provisional application No. 60/395,082, filed on Jul. 10, 2002.

(51) Int. Cl.
A61B 6/00 (2006.01)

(52) U.S. Cl. ......... 600/476; 600/407; 600/473; 600/477

(58) Field of Classification Search ........... 600/407, 600/473, 476, 477
See application file for complete search history.

(56) References Cited

U.S. PATENT DOCUMENTS

| 2,706,927 A | 4/1955 | Wood | 600/344 |
|---|---|---|---|
| 2,790,438 A | 4/1957 | Taplin et al. | 600/344 |
| 3,068,742 A | 12/1962 | Hicks, Jr. et al. | 600/339 |
| 3,412,729 A | 11/1968 | Smith, Jr. | 600/324 |
| 3,461,856 A | 8/1969 | Polanyi | 600/323 |
| 3,638,640 A | 2/1972 | Shaw | 600/323 |
| 3,704,706 A | 12/1972 | Herczfeld et al. | 600/324 |
| 3,709,612 A | 1/1973 | Clemens | 356/407 |
| 3,866,599 A | 2/1975 | Johnson | 600/342 |
| 3,994,585 A | 11/1976 | Frey | 356/40 |
| 3,998,550 A | 12/1976 | Konishi et al. | 356/39 |
| 4,014,321 A | 3/1977 | March | 600/319 |
| 4,029,085 A | 6/1977 | DeWitt et al. | 600/315 |
| 4,086,915 A | 5/1978 | Kofsky et al. | 600/330 |
| 4,119,406 A | 10/1978 | Clemens | 422/81 |
| 4,129,125 A | 12/1978 | Lester et al. | 600/484 |
| 4,138,727 A | 2/1979 | Mantz | 708/813 |
| 4,162,405 A | 7/1979 | Chance et al. | 424/9.6 |

(Continued)

OTHER PUBLICATIONS

U.S. Appl. No. 09/622,112, Chance.

(Continued)

*Primary Examiner* — Brian Casler
*Assistant Examiner* — James Kish
(74) *Attorney, Agent, or Firm* — Ivan David Zitkovsky

(57) ABSTRACT

A system and method for examining or imaging brain functions of a subject includes a light source and a light detector located on the exterior surface of the subject's head. The light source introduces transcranially optical radiation into the brain of a subject, and the light detector detects radiation that has migrated in a brain region from the light source to the detector. The system also provides brain stimulation and evaluates the detected radiation to determine a brain cognitive function of the subject. One embodiment of the system can detect a brain disorder. Another embodiment of the system can detect "deceit." In addition to the optical module, the system may include other optional modules such as an EEG module, an MEG module, a thermography module, a respiratory module, a skin conductivity module, and a blood pressure module.

32 Claims, 34 Drawing Sheets

U.S. PATENT DOCUMENTS

| | | | | |
|---|---|---|---|---|
| 4,167,331 A | 9/1979 | Nielsen | | 356/39 |
| 4,222,389 A | 9/1980 | Rubens | | 600/328 |
| 4,223,680 A | 9/1980 | Jobsis | | 600/324 |
| 4,224,948 A | 9/1980 | Cramer et al. | | 600/503 |
| 4,259,963 A | 4/1981 | Huch | | 600/359 |
| 4,266,554 A | 5/1981 | Hamaguri | | 600/323 |
| 4,281,645 A | 8/1981 | Jobsis | | 600/324 |
| 4,321,930 A | 3/1982 | Jobsis et al. | | 600/344 |
| 4,380,240 A | 4/1983 | Jobsis et al. | | 600/344 |
| 4,416,285 A | 11/1983 | Shaw et al. | | 600/339 |
| 4,447,884 A | 5/1984 | Wada | | 702/131 |
| 4,452,250 A | 6/1984 | Chance et al. | | 600/410 |
| 4,469,107 A | 9/1984 | Asmar et al. | | 600/494 |
| 4,510,938 A | 4/1985 | Jobsis et al. | | 600/344 |
| 4,515,165 A | 5/1985 | Carroll | | 600/475 |
| 4,576,173 A | 3/1986 | Parker et al. | | 600/317 |
| 4,612,938 A | 9/1986 | Dietrich et al. | | 600/476 |
| 4,648,892 A | 3/1987 | Kittrell et al. | | 65/387 |
| 4,655,225 A | 4/1987 | Dahne et al. | | 600/316 |
| 4,700,708 A | 10/1987 | New, Jr. et al. | | 600/331 |
| 4,714,341 A | 12/1987 | Hamaguri et al. | | 356/41 |
| 4,738,267 A | 4/1988 | Lazorthes et al. | | 600/561 |
| 4,773,422 A | 9/1988 | Isaacson et al. | | 600/326 |
| 4,774,679 A | 9/1988 | Carlin | | 702/41 |
| 4,800,495 A | 1/1989 | Smith | | 600/322 |
| 4,800,885 A | 1/1989 | Johnson | | 600/330 |
| 4,805,623 A | 2/1989 | Jobsis | | 600/328 |
| 4,807,637 A | 2/1989 | Bjorkholm | | 600/476 |
| 4,824,242 A | 4/1989 | Frick et al. | | 356/41 |
| 4,836,207 A | 6/1989 | Bursell et al. | | 600/318 |
| 4,846,183 A | 7/1989 | Martin | | 600/336 |
| 4,869,254 A | 9/1989 | Stone et al. | | 600/336 |
| 4,880,304 A | 11/1989 | Jaeb et al. | | 356/41 |
| 4,908,762 A | 3/1990 | Suzuki et al. | | 600/407 |
| 4,926,867 A | 5/1990 | Kanda et al. | | 600/334 |
| 4,937,526 A | 6/1990 | Ehman et al. | | 324/309 |
| 4,940,453 A | 7/1990 | Cadwell | | 600/13 |
| 4,951,682 A | 8/1990 | Petre | | 600/526 |
| 4,972,331 A | 11/1990 | Chance | | 600/310 |
| 5,035,243 A | 7/1991 | Muz | | 600/344 |
| 5,057,695 A | 10/1991 | Hirao et al. | | 250/575 |
| 5,062,431 A | 11/1991 | Potter | | 600/478 |
| 5,088,493 A | 2/1992 | Giannini et al. | | 600/323 |
| 5,090,415 A | 2/1992 | Yamashita et al. | | 600/476 |
| 5,106,387 A | 4/1992 | Kittrell et al. | | 606/15 |
| 5,119,815 A | 6/1992 | Chance | | 600/433 |
| 5,122,974 A | 6/1992 | Chance | | 600/323 |
| 5,137,355 A | 8/1992 | Barbour et al. | | 356/342 |
| 5,139,025 A | 8/1992 | Lewis et al. | | 600/477 |
| 5,143,081 A | 9/1992 | Young et al. | | 600/554 |
| 5,158,090 A | 10/1992 | Waldman et al. | | 600/473 |
| 5,174,298 A | 12/1992 | Dolfi et al. | | 600/425 |
| 5,178,142 A | 1/1993 | Harjunmaa et al. | | 600/310 |
| 5,187,672 A | 2/1993 | Chance et al. | | 600/407 |
| 5,190,039 A | 3/1993 | Takeuchi et al. | | 600/311 |
| 5,198,977 A | 3/1993 | Salb | | 382/128 |
| 5,203,339 A | 4/1993 | Knuttel et al. | | 600/425 |
| 5,213,105 A | 5/1993 | Gratton et al. | | 600/473 |
| 5,218,962 A | 6/1993 | Mannheimer et al. | | 600/331 |
| 5,257,202 A | 10/1993 | Feddersen et al. | | 702/32 |
| 5,277,181 A | 1/1994 | Mendelson et al. | | 600/322 |
| 5,287,276 A | 2/1994 | Crawford et al. | | 378/4 |
| 5,300,097 A | 4/1994 | Lerner et al. | | 607/93 |
| 5,309,907 A | 5/1994 | Fang et al. | | 600/342 |
| 5,309,912 A | 5/1994 | Knuttel | | 600/425 |
| 5,353,799 A | 10/1994 | Chance | | 600/473 |
| 5,358,503 A | 10/1994 | Bertwell et al. | | 606/27 |
| 5,402,778 A | 4/1995 | Chance | | 600/310 |
| 5,408,093 A | 4/1995 | Ito et al. | | 250/227.26 |
| 5,413,098 A | 5/1995 | Benaron | | 600/310 |
| 5,416,582 A | 5/1995 | Knutson et al. | | 356/484 |
| 5,431,170 A | 7/1995 | Mathews | | 600/479 |
| 5,494,032 A | 2/1996 | Robinson et al. | | 600/323 |
| 5,497,769 A | 3/1996 | Gratton et al. | | 600/323 |
| 5,551,422 A | 9/1996 | Simonsen et al. | | 600/322 |
| 5,551,423 A | 9/1996 | Sugiura | | 600/476 |
| 5,596,987 A | 1/1997 | Chance | | 600/310 |
| 5,625,458 A | 4/1997 | Alfano et al. | | 356/446 |
| 5,655,530 A | 8/1997 | Messerschmidt | | 600/366 |
| 5,673,701 A | 10/1997 | Chance | | 600/473 |
| 5,706,821 A | 1/1998 | Matcher et al. | | 600/310 |
| 5,779,631 A | 7/1998 | Chance | | 600/328 |
| 5,782,755 A | 7/1998 | Chance et al. | | 600/322 |
| 5,807,263 A | 9/1998 | Chance | | 600/476 |
| 5,845,639 A | 12/1998 | Hochman et al. | | 600/407 |
| 5,943,133 A | 8/1999 | Zeylikovich et al. | | 356/496 |
| 5,949,077 A | 9/1999 | Alfano et al. | | 250/459.1 |
| 5,954,053 A * | 9/1999 | Chance et al. | | 600/310 |
| 5,983,125 A | 11/1999 | Alfano et al. | | 600/473 |
| 5,987,351 A | 11/1999 | Chance | | 600/473 |
| 5,995,856 A | 11/1999 | Mannheimer et al. | | 600/322 |
| 6,006,001 A | 12/1999 | Alfano et al. | | 385/115 |
| 6,058,324 A | 5/2000 | Chance | | 600/473 |
| 6,091,983 A | 7/2000 | Alfano et al. | | 600/431 |
| 6,108,576 A | 8/2000 | Alfano et al. | | 600/476 |
| 6,201,989 B1 | 3/2001 | Whitehead et al. | | 600/476 |
| 6,215,587 B1 | 4/2001 | Alfano et al. | | 359/368 |
| 6,240,309 B1 * | 5/2001 | Yamashita et al. | | 600/407 |
| 6,996,256 B2 * | 2/2006 | Pavlidis | | 382/118 |
| 7,610,082 B2 | 10/2009 | Chance | | 600/475 |
| 2002/0099295 A1 | 7/2002 | Gil et al. | | |
| 2003/0012253 A1 | 1/2003 | Pavlidis | | |
| 2003/0073910 A1 | 4/2003 | Chance | | 600/473 |
| 2005/0154290 A1 * | 7/2005 | Langleben | | 600/410 |

OTHER PUBLICATIONS

U.S. Appl. No. 09/622,184, Chance.

* cited by examiner

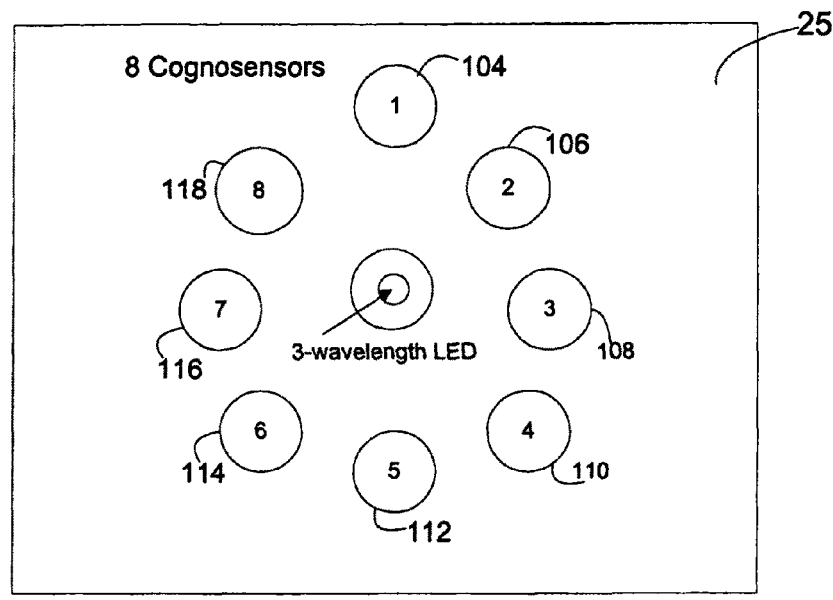
FIG. 2
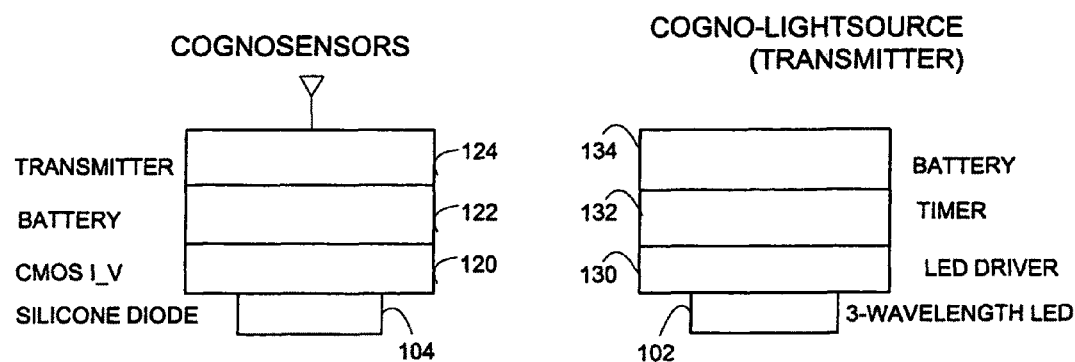
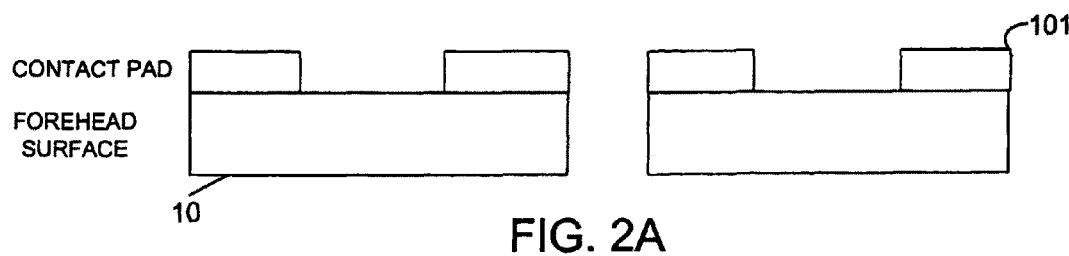
FIG. 2A

Receiver System Diagram

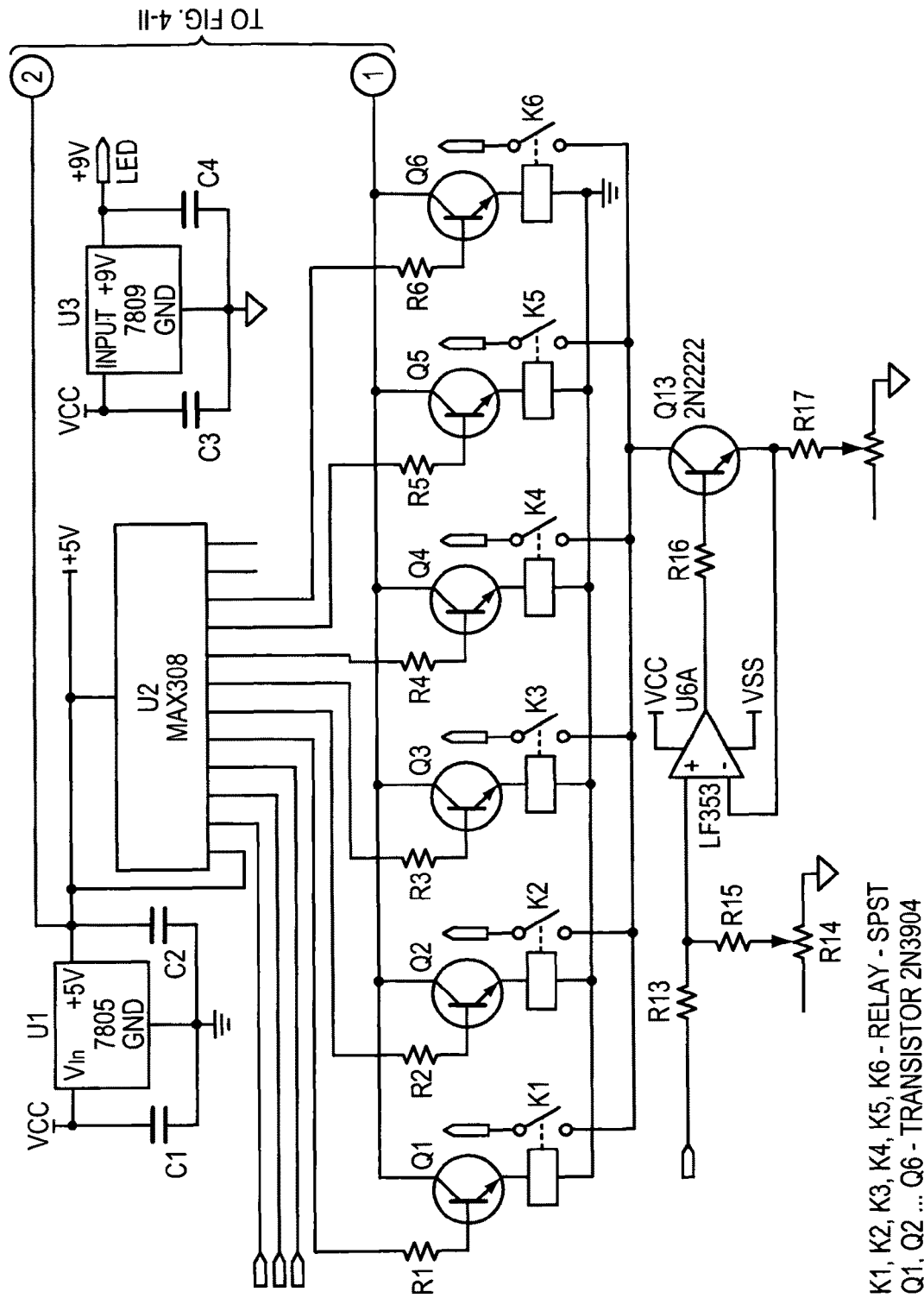
FIG. 4-I

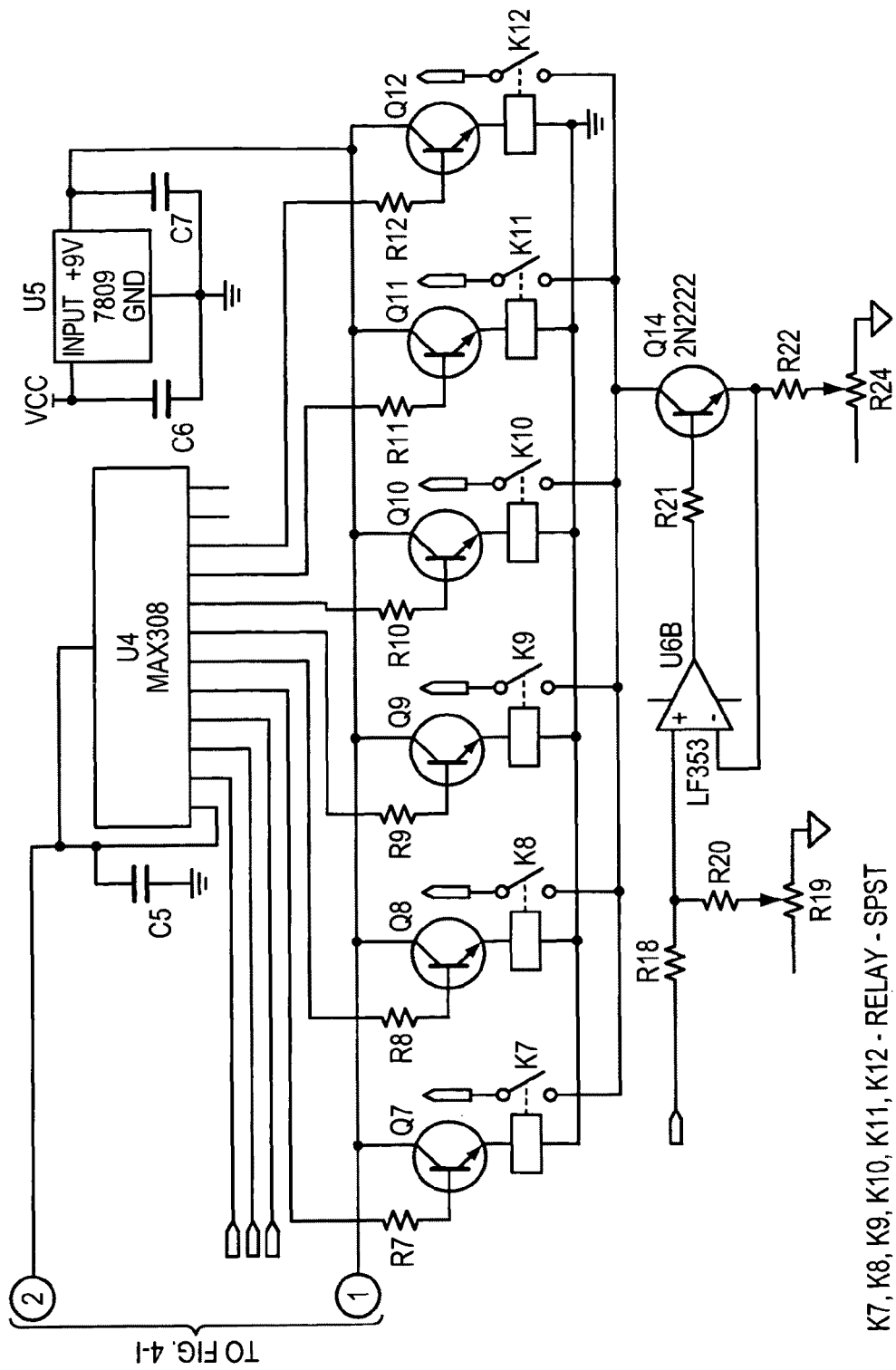
FIG. 4-II

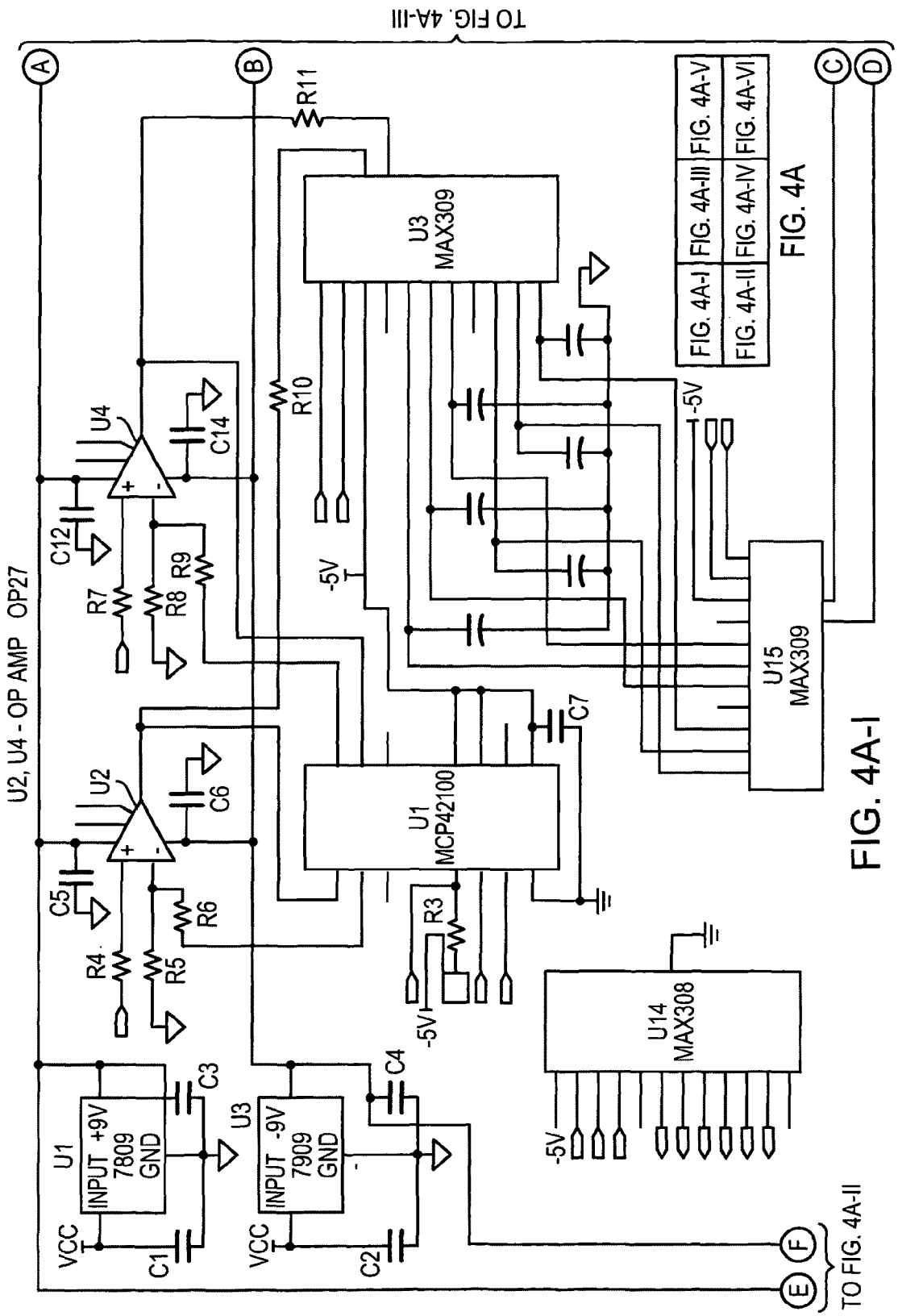
FIG. 4A-I

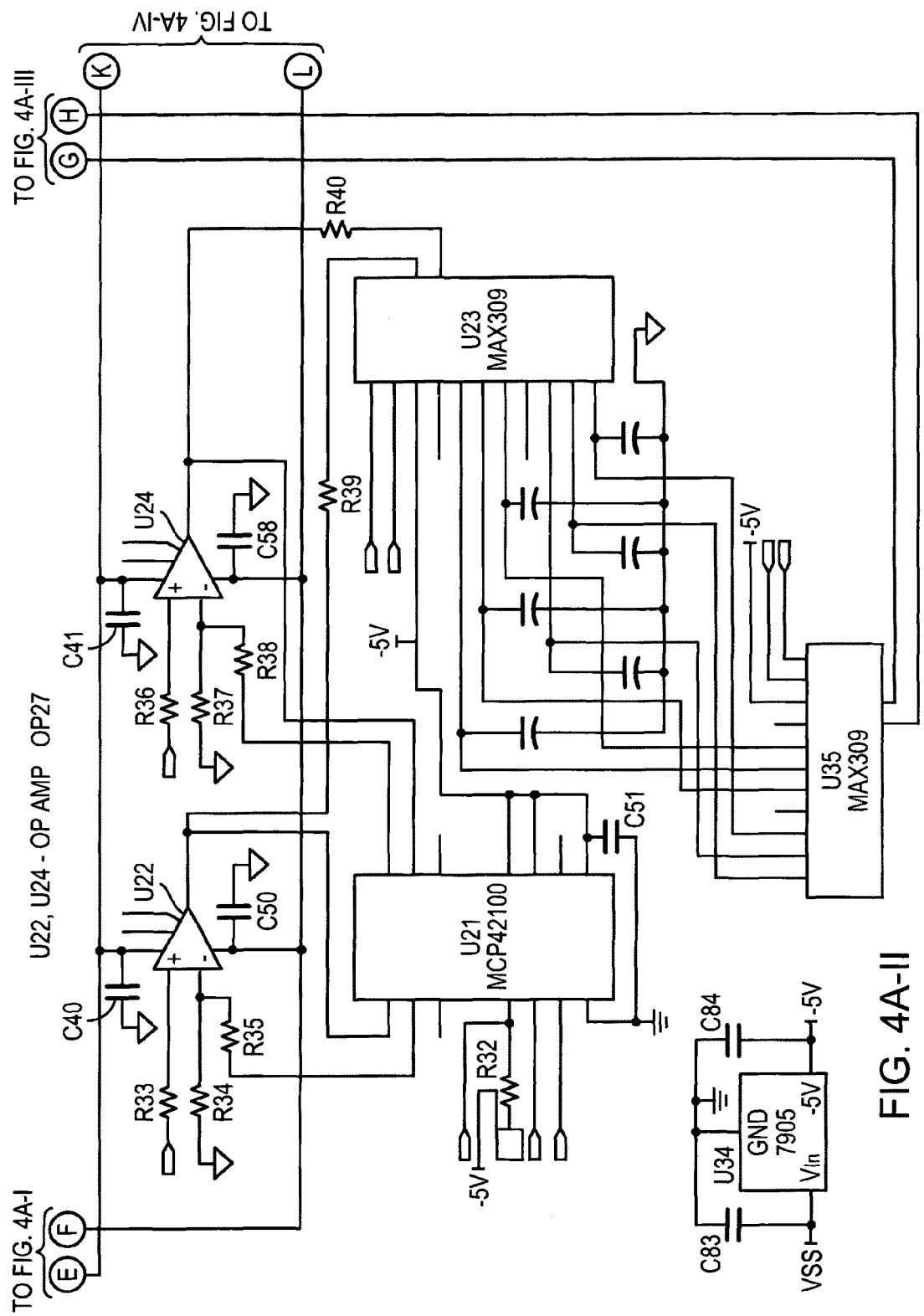
FIG. 4A-II

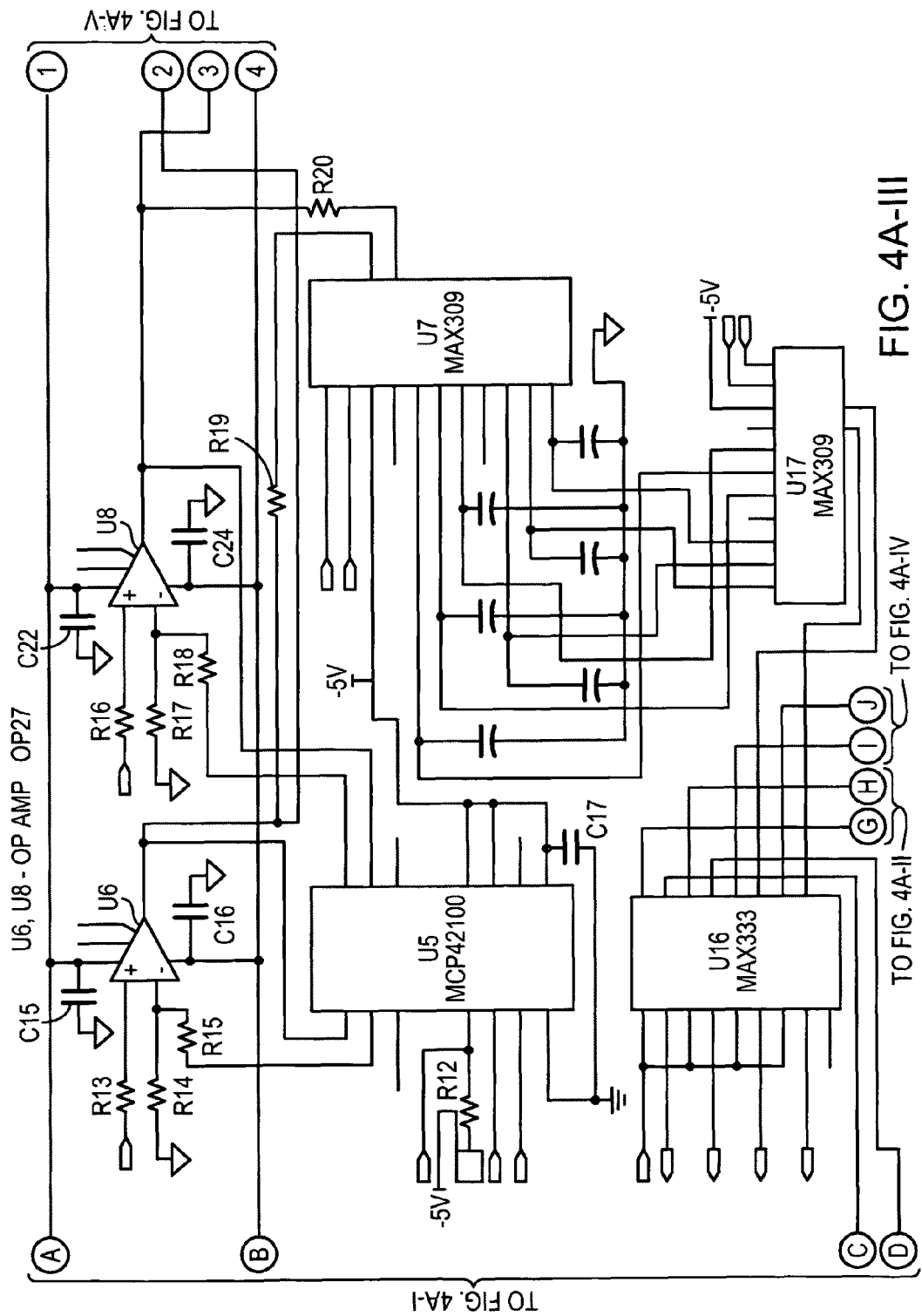
FIG. 4A-III

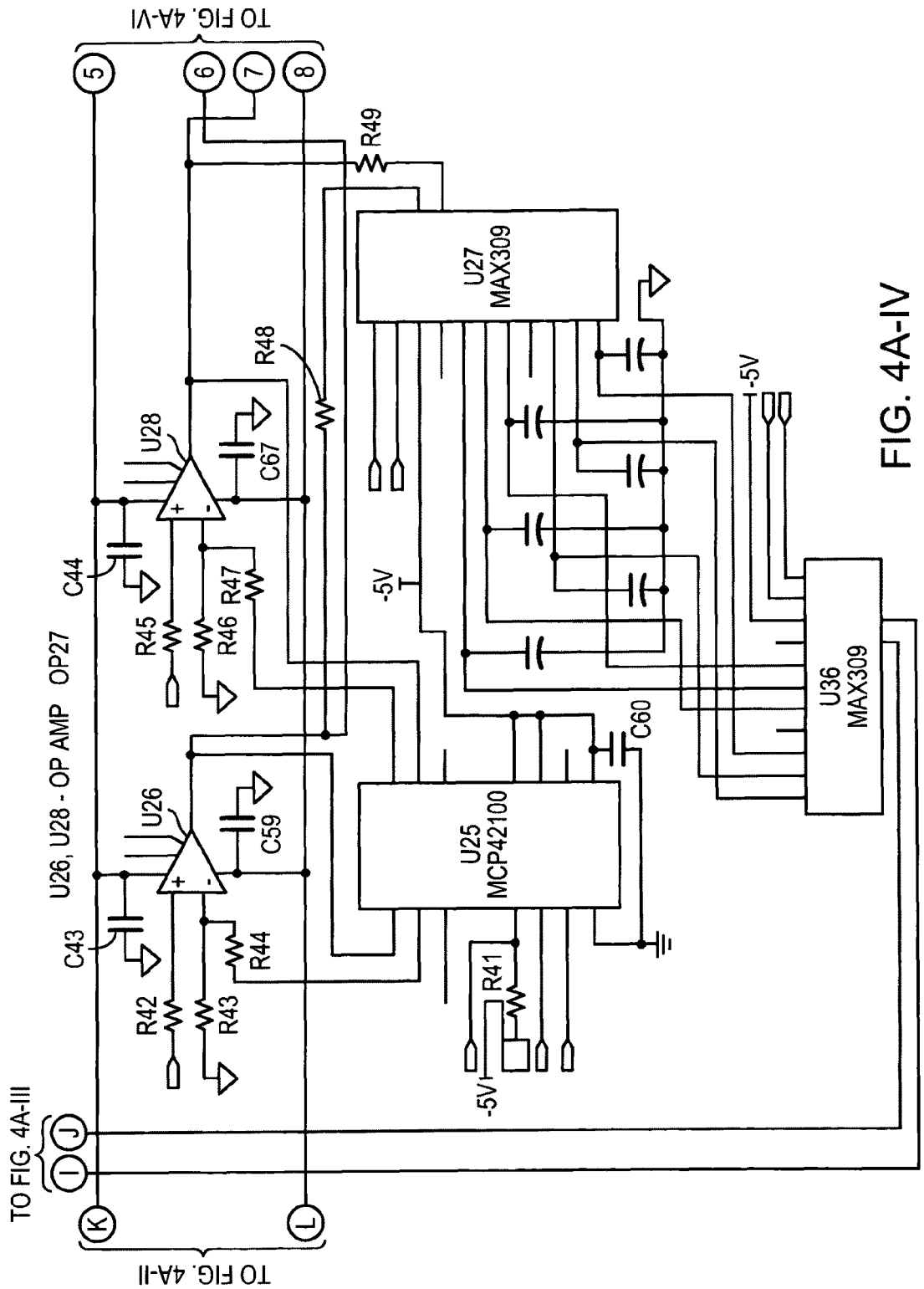
FIG. 4A-IV

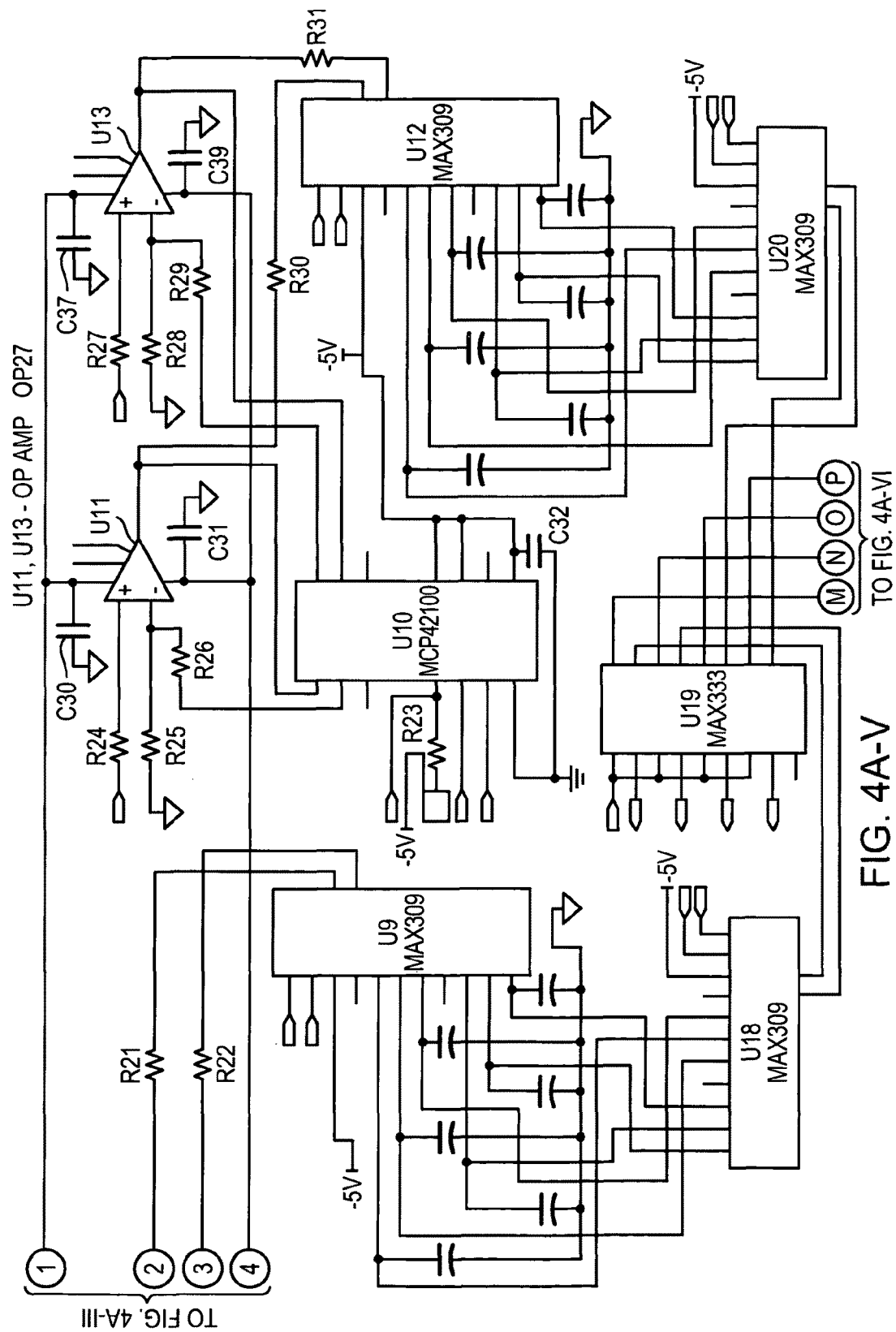

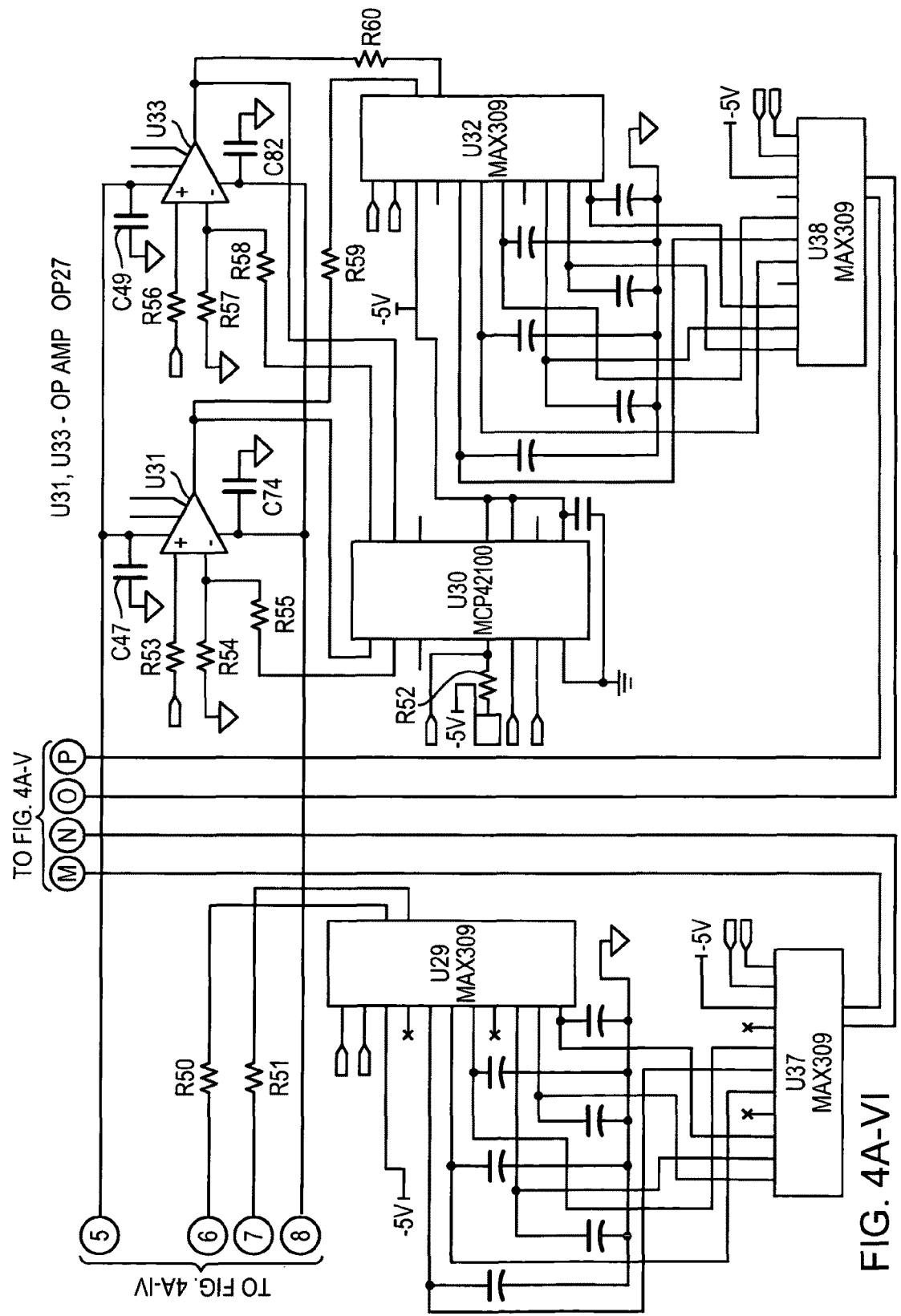
FIG. 4A-VI

POST 5-LETTER ANAGRAMS
614 SOLUTIONS

PRE 5-LETTER ANAGRAMS
326 SOLUTIONS

OXYGENATION CHANGES

BLOOD VOLUME CHANGES

EVENT RELATED IMAGE:
15 SECONDS AFTER SUDDEN INSIGHT MINUS
15 SECONDS BEFORE SUDDEN INSIGHT

OXYGENATION

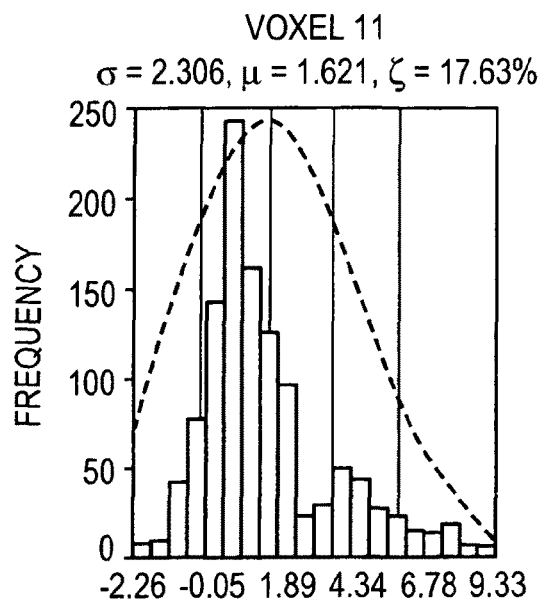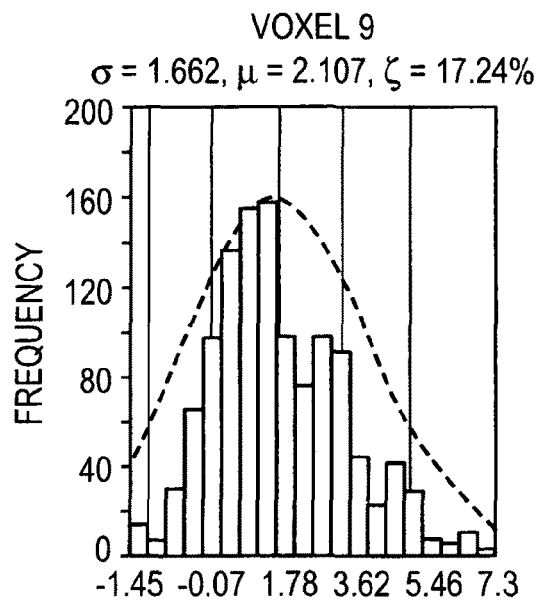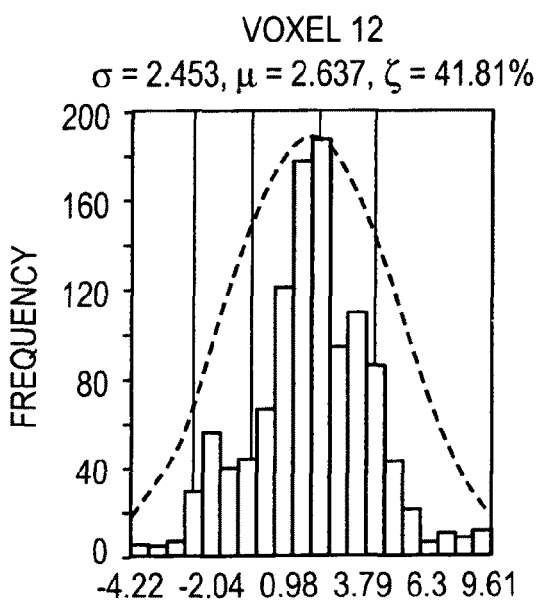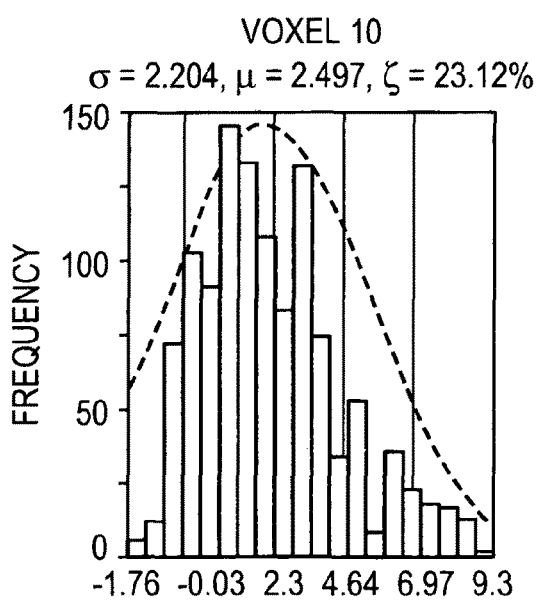
FIG. 10C

5-letter Anagram Solutions
8-letter Anagram Solutions
BV magnitudes, Max=10
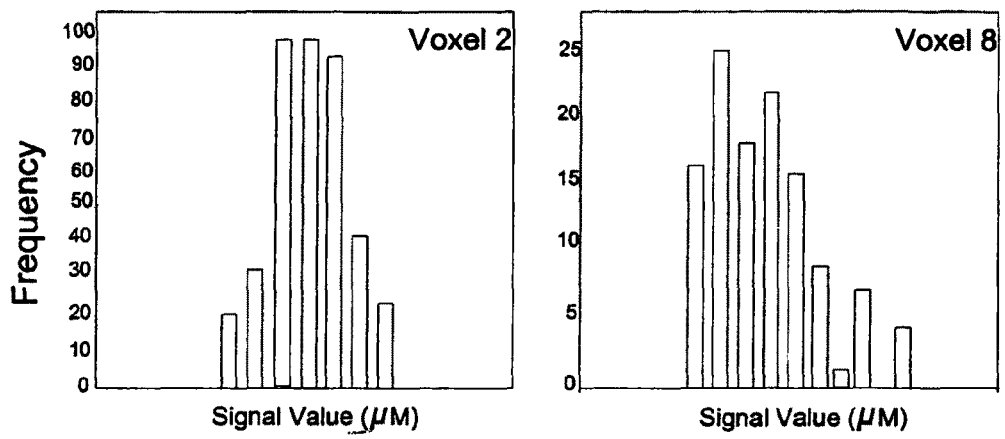
Oxy magnitudes, Max=10
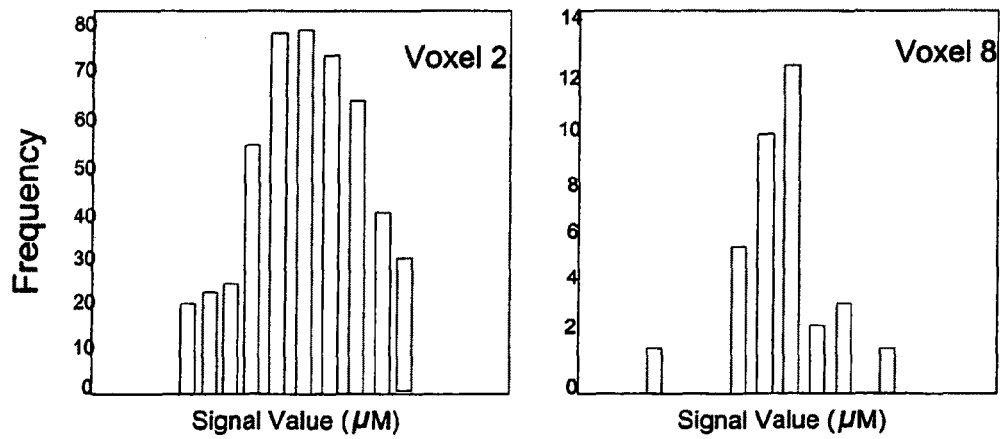
FIG. 12

EXAMINATION AND IMAGING OF BRAIN COGNITIVE FUNCTIONS

This application is a continuation of U.S. application Ser. No. 10/752,440, filed on Jan. 5, 2004, now U.S. Pat. No. 7,840,257 entitled "Examination of Biological Tissue using Non-Contact Optical Probes," which claims priority from U.S. Provisional Application 60/438,229, filed on Jan. 4, 2003; and this application is also a continuation of U.S. application Ser. No. 10/618,579, filed on Jul. 10, 2003, now abandoned entitled "Examination and Imaging of Brain Cognitive Functions," which claims priority from U.S. Provisional Application 60/395,082, filed on Jul. 10, 2002, all of which are incorporated by reference.

The present invention related to examination of brain cognitive functions and processes using optical and other techniques.

BACKGROUND OF THE INVENTION

The human brain has been the object of many methodologies and hypotheses. The burgeoning technologies now available have each opened particular facets of the study, MRI being the most versatile as capable of imaging hemodynamic and metabolic signals in a unique fashion. PET has similar possibilities of large chemical specificity governed by the combination of lifetimes and radiation from radioactive isotopes. Other methods give highly specialized signals, for example, MEG and EEG that have respectively high and low resolution for neurophysiological signals. Optical tomography is somewhat more quantitative with respect to hemodynamic changes and has latent possibilities for measuring neuronal signals. The propagation of near infrared light through biological tissue such as the brain and breast has been experimentally studied and theoretically modeled. Accurate theoretical models are based on Monte Carlo representations of the diffusion equation and on analytic expressions that show propagation into the gray matter of the brain in adults and especially in neonates. This propagation of light into cranial tissue has been verified by clinical measurement of the presence of X-ray CT identified cranial hematomas at depths 3-4 cm. Detection of the oxygenation state and amount of hemoglobin has been the goal of tissue oximetry and quantitative results are obtained by time and frequency domain devices. These devices measure the optical pathlength over which photons diffuse from source to detector. However, single volume determination of optical parameters of a highly heterogeneous system such as the human brain may give only a fraction of the signal of a localized focal activation already shown to be highly localized by ƒMRI (functional Magnetic Resonance Imaging).

The optical systems are relatively simple, safe, portable and affordable as required by today's health care industry. There are several optical examination and imaging devices that have been used for imaging functional activity of adult, full-term and pre-term neonate brain. These optical examination and imaging systems are described in U.S. Pat. Nos. 5,353,799; 5,853,370; 5,807,263, 5,820,558. The described optical systems do not require subject immobilization (as do MRI and PET). The images are acquired in less than half a minute and show good two-dimensional resolution of blood changes.

The amplitude and phase cancellation devices have been used to study the prefrontal region of adults and the parietal region of pre-and full-term infants and have been used for the detection of breast tumors. In addition to the use of phase and amplitude cancellation, there are two general principles for object detection in the biological tissue. In brain examination, an optical system can use the difference between rest and functional activation since the transition time between the two states of the brain function is several seconds. The second principle is used, where symmetry exists such as in the hemispheres of the brain or in the human breasts. The symmetric "lateralization" signal has been used to detect brain bleeds and breast tumors since it enables cancellation unwanted background signals.

Phase cancellation systems use preferably an arrangement of detectors and equidistant sources from which amplitude and phase cancellation may be obtained. If equal light amplitudes at 0 and 180° phases are used for the light sources, an appropriate positioning of the detector can lead to a "null" in the amplitude signal and a crossover between 0 and 180° phase shift, i.e., 90°. In homogeneous tissue, this null is symmetrically in the middle. In heterogeneous tissue, this null may is displaced from the geometric midline. Thus, the null establishes an extremely sensitive measure to perturbation by an absorber or scatterer. The detection sensitivity can be further increased by using a NIR absorbing dye such as indocyanine green (ICG) administered or injected in the tissue. Advantageously, the null location is relatively insensitive to amplitude fluctuations common to both light sources, and is insensitive to inhomogeneities that affect a large tissue volume common to the two optical patterns. Sensitivity to scattering is high particularly provided that the scattering contrast is the same as the absorbing contrast. The crossover signal is preferably used for imaging. The amplitude signal is somewhat less useful for imaging since the position indication is ambiguous, i.e., an increase of signal is observed regardless of the displacement of the absorbing object away from to the null plane. However, this can be accounted for by software corrections.

The optical phase system generates a photon diffusion wave of a long wavelength (~10 cm) as determined by the particular scattering ($\mu_s$=10 cm$^{-1}$) and absorbing ($\mu_a$=0.04 cm$^{-1}$) properties of the medium and the radio-frequency (~100 MHz). Optical wavelengths in the visible to infrared range, preferably between 700-850 nm are determined by the availability of laser diodes. Thus the photon diffusion wavelength of ~10 cm provides imaging in the "near field", and diffraction effects are absent. The phase signal at zero crossing detection is essentially a square wave "overloaded" signal. It is moderately insensitive to the changes of signal amplitude that may occur in imaging from proximal to distal source-detector pairs and is also little insensitive to ambient light.

There is still a need for optical examination and imaging systems for examining various brain cognitive functions and processes.

SUMMARY OF THE INVENTION

The present invention is a method and system for examination and imaging of brain cognitive functions.

According to one aspect, system and method for examining a brain function of a subject introduces optical radiation from a light source into the brain of a subject and detects radiation that has migrated in a brain region from the light source to a detector. The system also provides brain stimulation while introducing and detecting the optical radiation, and stores the detected radiation to create optical data. The system then evaluates the optical data to determine a brain function of the subject.

According to another aspect, system and a method for detecting deceit by a subject introduces optical radiation from a light source into the brain of a subject and detects radiation that has migrated in a brain region from the light source to a detector. The system also provides brain stimulation and receives a response from the subject while introducing and detecting the optical radiation, and stores the detected radiation to create optical data. The system then evaluates the optical data to determine whether the response was a knowingly false response.

The brain stimulation includes visual stimulation, auditory stimulation or any other stimulation that stimulates cognitive function of the brain or stimulates memories stored in the brain. The visual stimulation may include displaying a picture or displaying a movie.

The light source may include a light emitting diode (LED), a laser diode or a halogen or tungsten light bulb. The light source may provide a single wavelength or multi-wavelength light and may include a filter. The light detector may include a photodiode (e.g., a Si diode, PIN diode, avalanche diode), a photoresistor, a photomultiplier tube (PMT), or a CCD device.

The introduction and detection of optical radiation may be performed while providing the brain stimulation. The introduction and detection of optical radiation may be performed without the brain stimulation to obtain "background" optical data. The introduction and detection of optical radiation may be performed to obtain "rest" optical data at a low level of the brain stimulation, and the introduction and detection of optical radiation may be performed to obtain "functional" optical data at a high level of the brain stimulation. For example, the low level of the brain stimulation may include solving a simple mathematical problem or an anagram having three or four letters. The high level of the brain stimulation may include solving a difficult mathematical problem or an anagram having 8 to 12 letters. Alternatively, the low level of the brain stimulation may include asking simple every-day questions, and the high level of the brain stimulation may include asking "uncomfortable" or incriminating questions.

The optical data may include blood volume or blood oxygenation. The optical data may be displayed in form of standard images using, for example a back projection algorithm. The optical data may be displayed in form of "images" including relative or differential data. The optical data are displayed in form of histograms for the individual brain regions.

The system evaluates the examined brain function or the veracity of the subject's response an optical signature alone or in combination with a non-optical signature. The optical signature is based on the optical data (e.g., blood volume or blood oxygenation). The non-optical signature is based on the non-optical data measured by an EEG module, a MEG module, a thermography module, a respiratory module, a skin conductivity module, or a blood pressure module. The optical signature may include a specific or identifiable signature voxel (e.g., a fruitful voxel). The optical signature may include other measures such as intensity, gradient or a relative value derived from the optical data. The optical signature may also include a histogram or a "statistical" value or factor obtained by evaluating a large number of optical data sets. Each optical data set can be based on the blood volume data or the blood oxygenation data, or the congruence of blood volume and blood oxygenation. The optical data sets can be acquired over a short or a long period of time (including training time). Various optical data sets can be acquired while initiating a low level of the brain stimulation or a high level of the brain stimulation.

One embodiment of the system can evaluate a specific brain function or detect a brain disorder (e.g., attention deficit disorder). Another embodiment of the system can detect "deceit." The evaluated brain function may include an emotional response, wherein the emotional response is a signature of propensity to violent behavior, or wherein the emotional response is a signature of propensity to antisocial behavior. The present system and method can be used to detect disattention, a learning ability, or other cognitive processes, including diminished or absent processes.

In the present systems, the brain function is characterized based on detecting an optical signature, which is related to the existence of one or several signature voxels (i.e., "fruitful voxels). Furthermore, as described below, at the moment of solving a "cognitive" problem (such as a math problem or an anagram) the sudden insight or the "eureka" moment, the optical system detects a pronounced dip and a rise in the blood volume signal.

The optical system can measure emotional response to displayed or stimulated situations by subtracting the optical signal corresponding to distress (e.g., a violent scene) and normal "calm" signal (e.g., a pastoral scene signal). Thus, the described systems can be used as "violence measure detectors" when properly "trained" and calibrated Furthermore, the described systems can be used as "deceit measure detectors" by generating optical images. Depending on the "background" images, the detected optical images provide a strong signal at one, two or three signature voxels when the subject is telling the truth, and provide weak signal at the signature voxel (relative to other voxels) when the subject is lying. Based on the optical images, a "deceit" level is evaluated. The optical deceit data can be combined with other non-optical data measured of the subject to calculate the "deceit" level.

BRIEF DESCRIPTION OF THE DRAWINGS

FIG. 2 shows schematically an optical probe for brain examination and imaging.

FIG. 2A shows schematically elements of the optical probe shown in FIG. 2.

FIGS. 4A-I, 4A-II, 4A-III, 4A-IV, 4A-V and 4A-VI show a circuit diagram of a signal processing circuit for 12 diode detectors.

FIGS. 4A-I and 4A-II show a circuit diagram of a signal processing circuit for 12 diode detectors.

FIGS. 10A, 10B, 10C and 10D shows optical data plotted in form of histograms for individual voxels corresponding to brain regions in the prefrontal area activated while solving anagrams.

FIG. 12 shows histograms for the blood volume and oxygenation signals plotted for two selected voxels.

DESCRIPTION OF PREFERRED EMBODIMENTS

Figure 1:
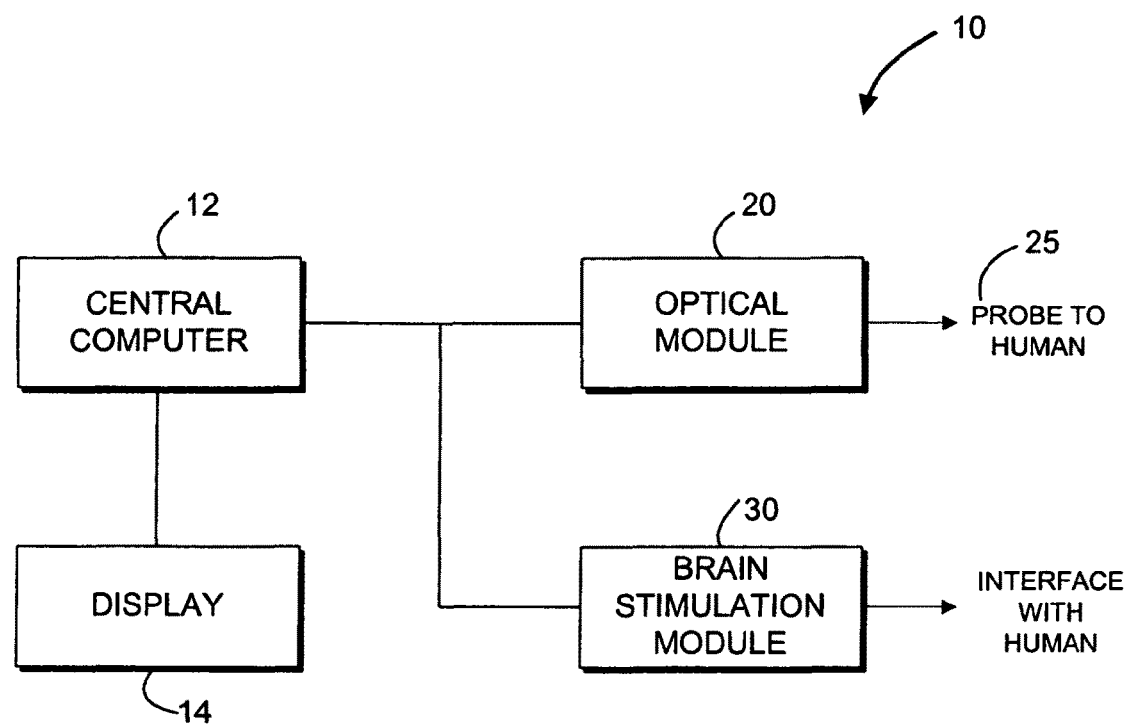
FIG. 1 shows schematically a brain examination and imaging system.

FIG. 1 shows schematically an optical system 10 for examination or imaging of brain functions. Optical system 10 includes a central computer 12, a display 14, an optical module 20, and a brain stimulation module 30. Various embodiments of optical module 20 are described in U.S. Pat. Nos. 5,353,799; 5,853,370; 5,807,263; 5,820,558 all of which are incorporated by reference. Additional embodiments of optical module 20 are described in PCT Applications PCT/US99/03030; PCT/US99/03099; PCT/US99/02953 all of which are incorporated by reference.

Figure 3:
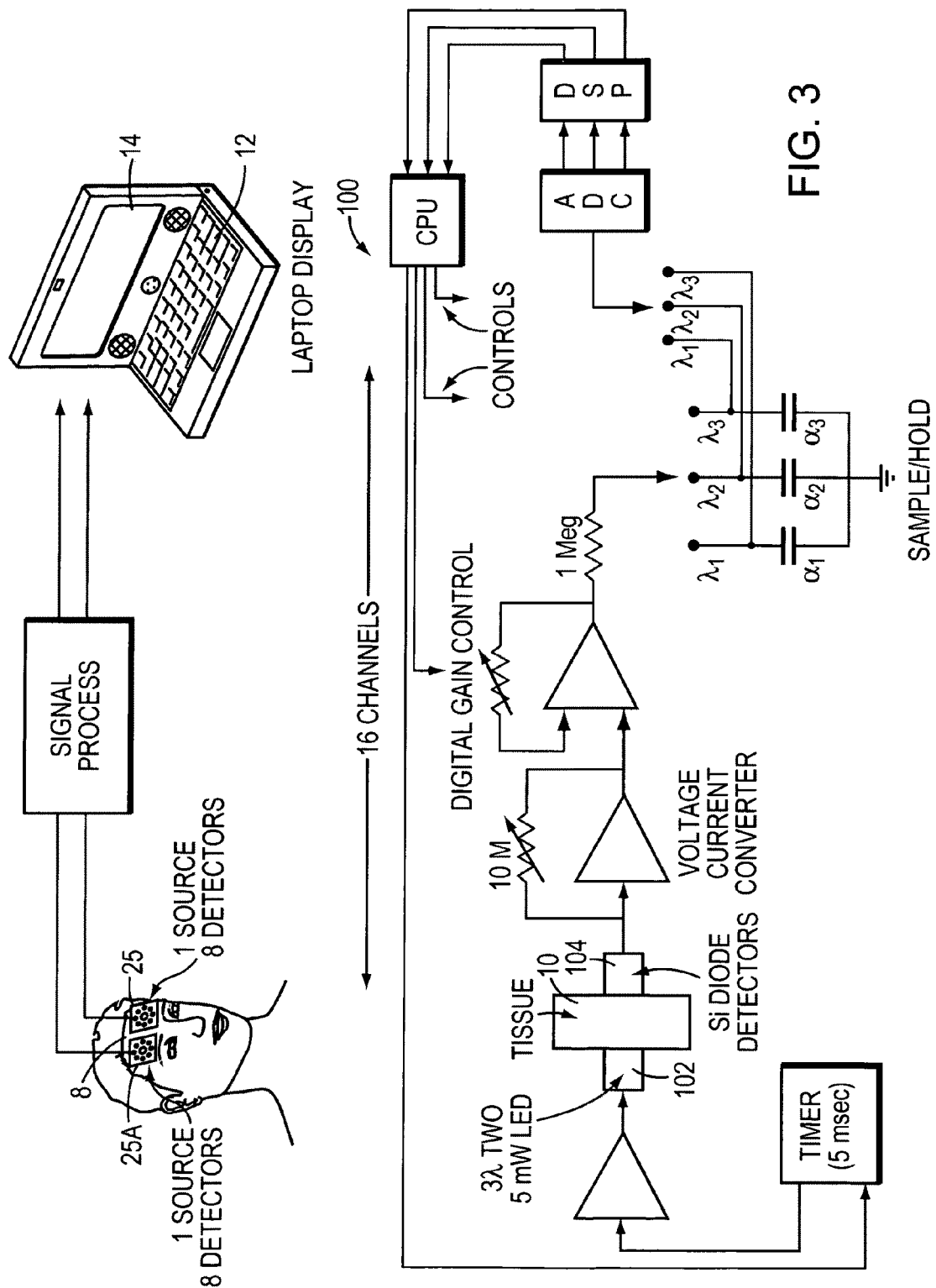
FIG. 3 shows schematically a three-wavelength optical module used in the systems of FIG. 1, 1A or 1B.
Figure 3A:
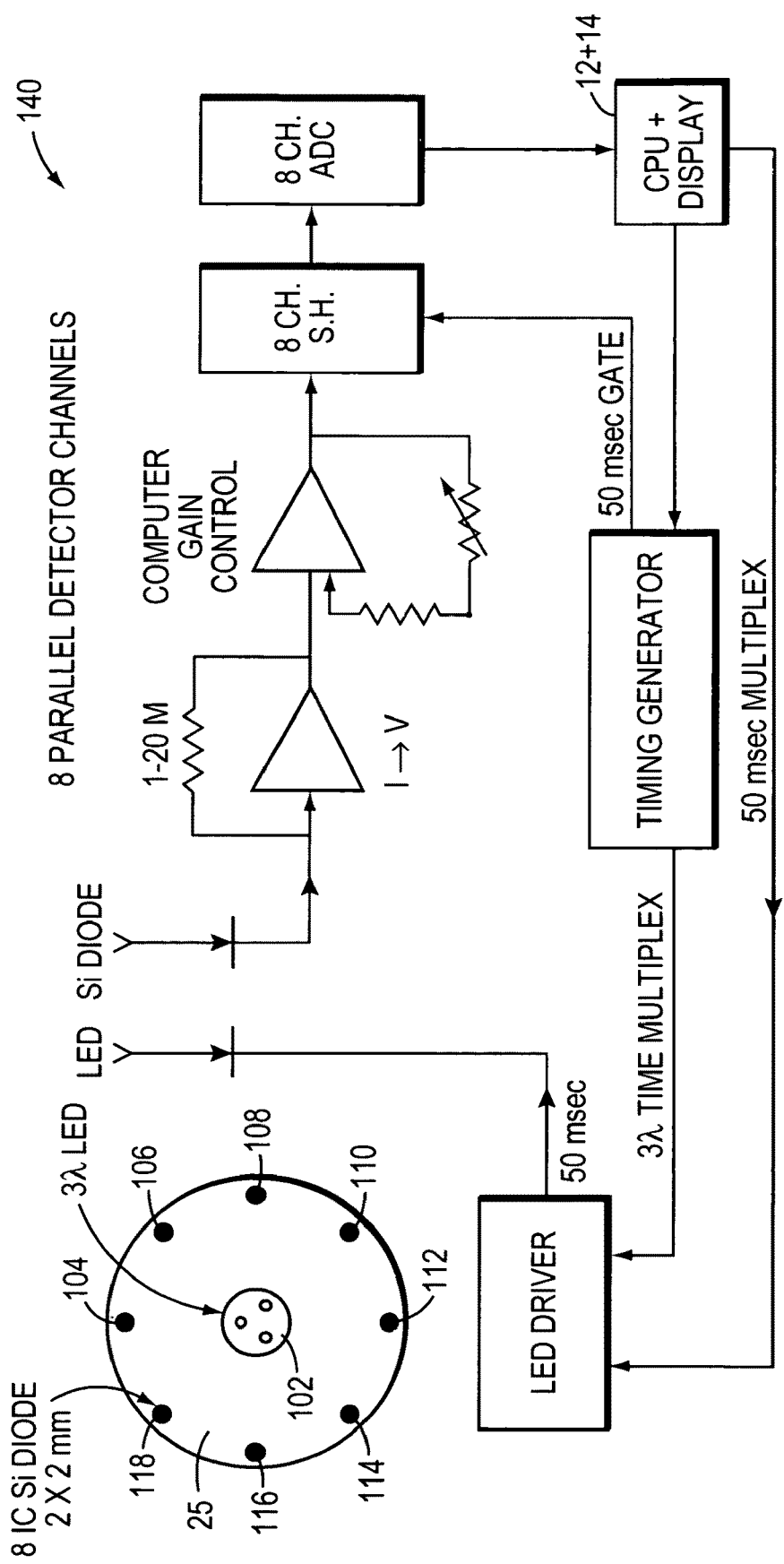
FIG. 3A shows schematically another embodiment of the three-wavelength optical module used in the systems of FIG. 1, 1A or 1B.
Figure 3B:
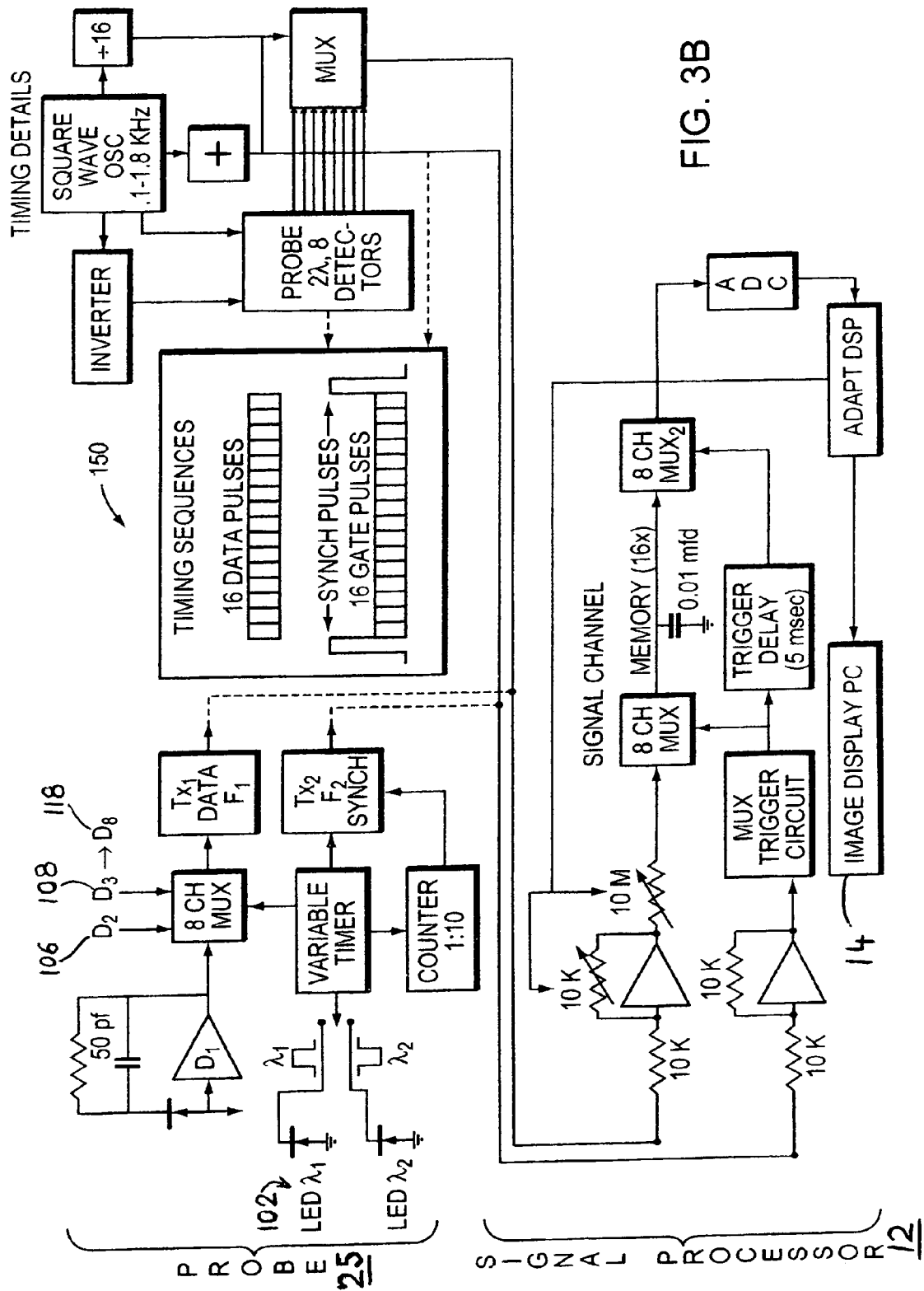
FIG. 3B show schematically another embodiment of the optical module used in the systems of FIG. 1, 1A or 1B.

Preferred embodiments of optical module 20 are described and shown in FIGS. 3, 3A and 3B. Optical module 20 includes an optical probe and the corresponding control and processing electronics. Brain stimulation module 30 is constructed to stimulate a specific cognitive or neural function of a subject. Brain stimulation module 30 may be controlled by computer 12 constructed to also control optical module 20 and achieve desired correlation between the modules. Brain stimulation module 30 can emits light, display pictures or written massages, emit sound or provide other signals for stimulating cognitive processes. Brain stimulation module 30 may also include an interface for receiving signals from a subject using mechanical, electrical, thermal, sound or light signals. In general, brain stimulation module 30 can be constructed to provide mechanical, electrical, thermal, sound or light signals designed to stimulate the cognitive or neural activity of interest. This activity is induced by sensory stimuli, such as visual, auditory, or olfactory stimuli, taste, tactile discrimination, pain and temperature stimuli, or proprioceptive stimuli.

Figure 1A:
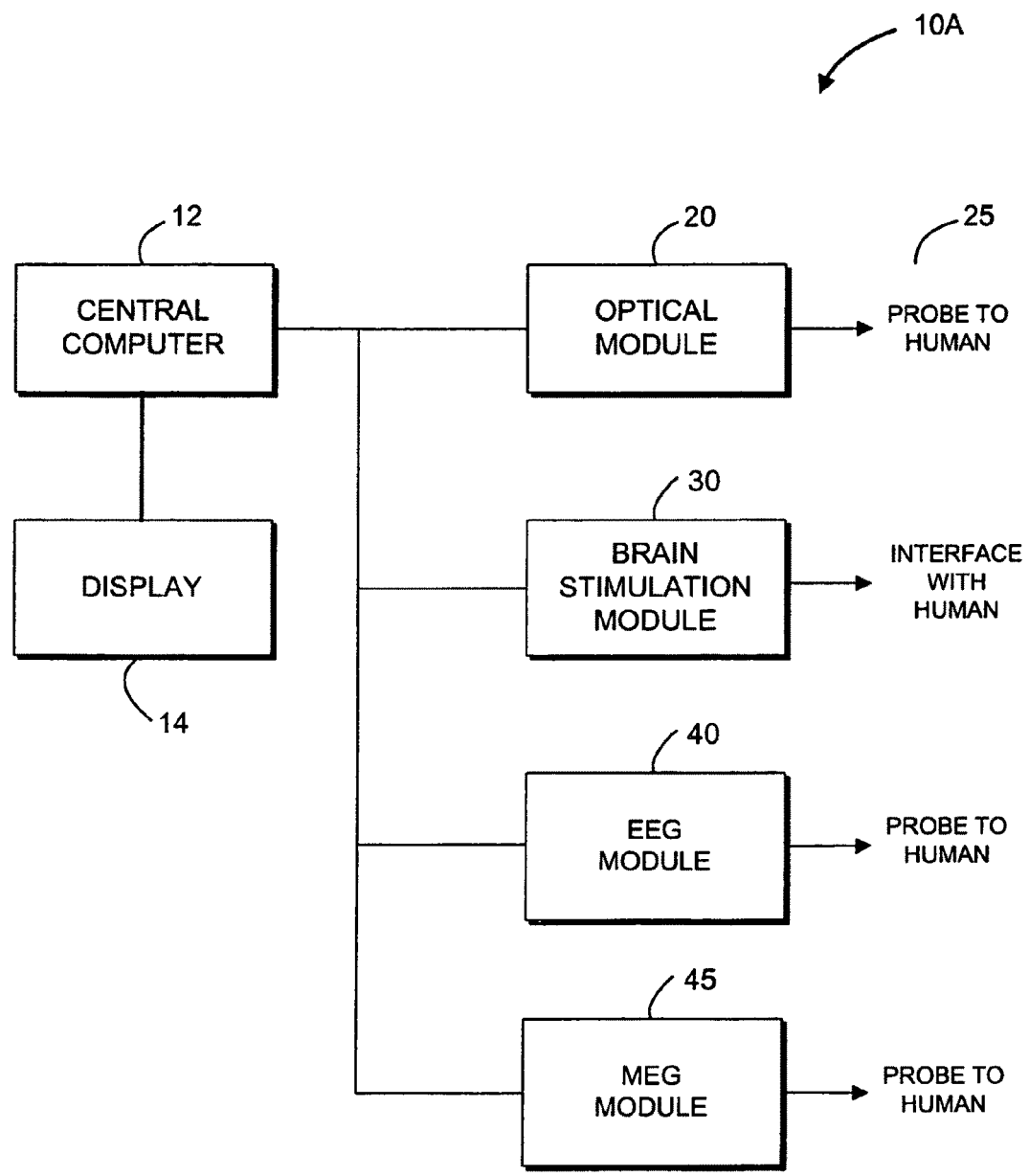
FIG. 1A shows schematically a combined optical and EEG or MEG brain examination and imaging system.

FIG. 1A shows schematically a combined system 10A, which includes an optical module, a brain stimulation module 30 and EEG system 10A for examination of brain activity. Combined optical and EEG system 10A includes a central computer 12, a display 14, an optical module 20, a brain stimulation module 30, an EEG module 40 and/or MEG module 45. Each module includes a probe or an interface with a human subject.

EEG module 40 is connected to an ECI electro-cap or another set of probes for measuring brain wave activity. The system can monitor a selected number of scalp locations. For example, EEG module 40 monitors up to nineteen scalp locations (Fp1, Fp2, F3, F4, F7, F8, T3, T4, T5, T6, C3, C4, P3, P4, O1, O2, Fz, Cz and Pz). All leads can be referenced to linked ear lobes (A1 and A2) and a ground electrode can be applied to the forehead. The system can also record vertical eye movements with electrodes placed above and below the eye. The 19 EEG traces can be digitized online at 500 Hz with a gain of 1000 (resolution of 0.084 µV/bit) and stored on a hard disk.

The 19 EEG traces are analyzed by any method known in the art. Prior to analysis a correction for ocular artifacts can be performed. The data can be divided into 2-second epochs (1024 data points), and automatically screened for artifacts. Excluded were all epochs showing amplitudes above ±100 µV. For each condition a Fast Fourier Transformation (FFT) can be performed on artifact-free 2-second chunks of data to derive estimates of absolute spectral power (µV) in different frequency bands. EEG module 40 can use, as a characteristic signature, the alpha band, which is believed to be inversely related to mental effort. The lower alpha band is primarily associated with attentional processes, whereas the upper alpha band is primarily associated with semantic memory processes. Central computer correlates signals from optical module 20, brain stimulation module 30, and EEG module 40 according to a selected algorithm and provides data corresponding to a selected brain activity.

Figure 1B:
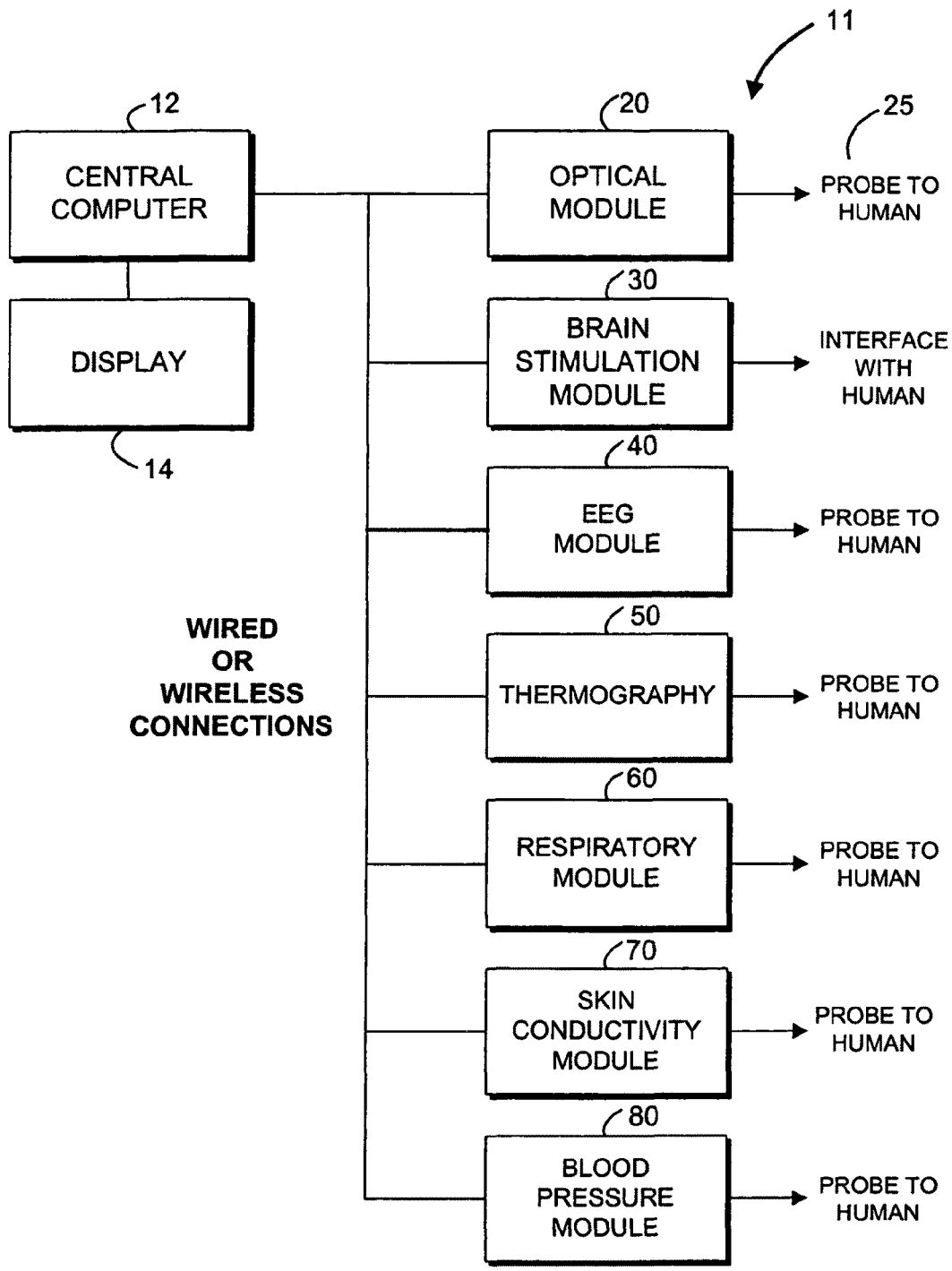
FIG. 1B shows schematically a deceit system including several modules for examining brain activity and evaluating veracity of human responses.

FIG. 1B shows schematically a polygraph system 11 including several modules. Polygraph system 11 includes central computer 12, display 14, optical module 20, brain stimulation module 30, EEG module 40, a thermography module 50, a respiratory module 60, a skin conductivity module 70, and a blood pressure module 80. The use of one or several of the above-listed modules is optional. Optical module 20 and brain stimulation module 30 are the primary modules for providing primary data that can be correlated with secondary data provided by modules 40 through 80.

As described below, optical module 20 can be used as "deceit measure detectors" that provides strong signal at a signature voxel when the subject is lying and provides weak signal at a signature voxel when the subject is telling the truth. This optical data may be correlated with non-optical data. The correlated data improves the sensitivity and scoring process and increases the accuracy of the results.

Polygraph system 11 may also include a volumetric module. The volumetric module uses a blood pressure cuff, as its probe, placed on the arm over the brachial artery and inflated to about 60 or 70 mm Hg pressure for an indirect measure of blood pressure. Blood pressure module 80 provides direct blood pressure measurements. The blood pressure measurements together with the strength and the pulse rate are provided to central computer 12. Thermography module 50 measures or maps the temperature of a subject during brain stimulation such as questioning, image projection, auditory or other stimulation.

Respiratory module 60 uses a respiratory probe including one or several rubber tubes placed around the subject. These rubber tubes measure expansion and contraction in the thoracic and abdominal areas of the subject. The resulting data depends on the gaseous exchange of the human during the respiratory process.

Skin conductivity module 70 includes several electrode probes attached to the skin and a galvanometer or another similar device for recording skin conductance or resistance to an electrical current. The measured skin conductance or resistance depends on the eccrine gland activity of the subject during brain stimulation.

In polygraph 11 (FIG. 1B), central computer 12 receives the individual input signals and provides the probability of deception. The individual digitized signals are transformed into more fundamental signals, correlated with the signals acquired during "background stimulation" and "examination stimulation". The standardized signals have their characteristic features compared to provide the deception output. Several modules and corresponding signal processing is described in U.S. Pat. No. 5,327,899, which is incorporated by reference.

Figure 2B:
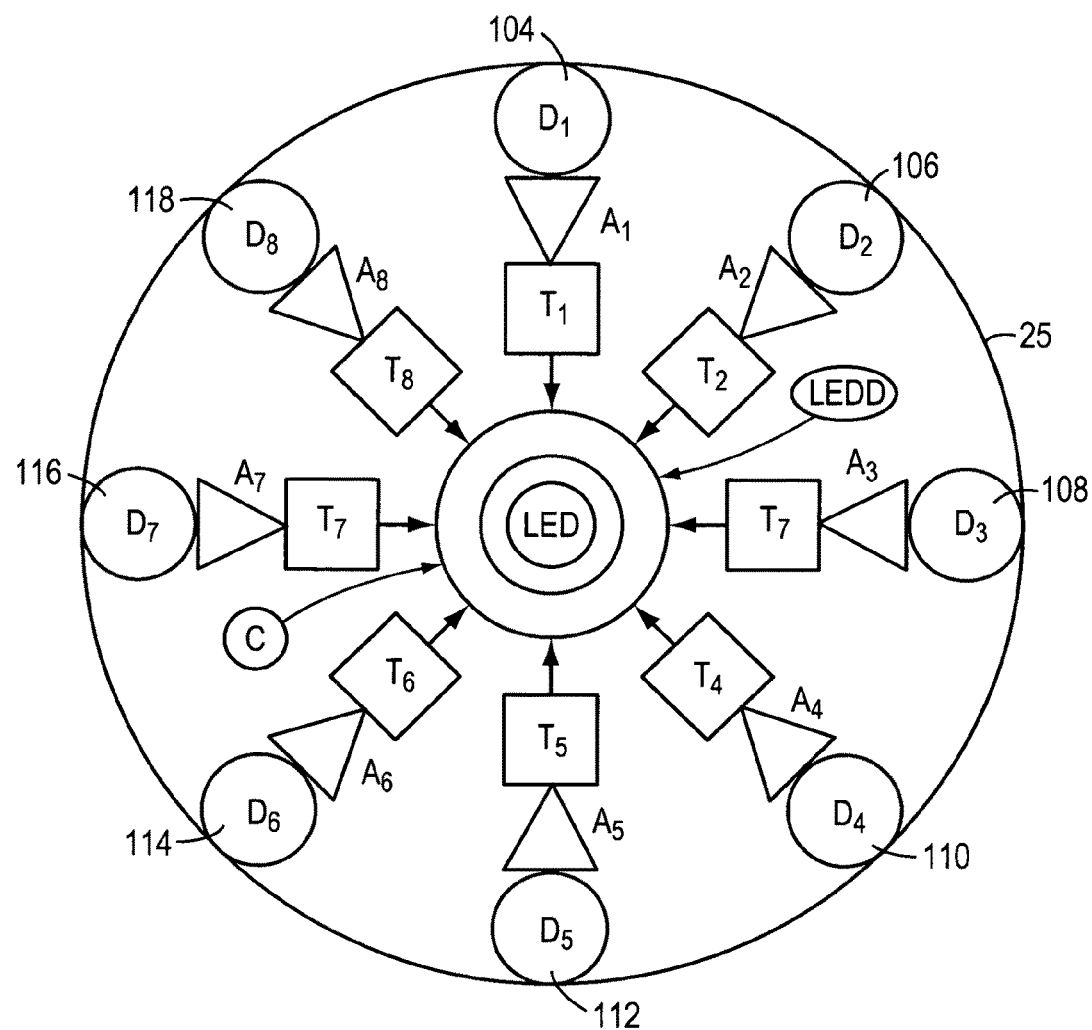
FIG. 2B shows schematically another arrangement of the optical probe of FIG. 2.

FIG. 2 shows schematically an optical probe 25 for brain examination and imaging. Optical probe 25 has two preferred embodiments. The first is a "hard-wired" embodiment (i.e., tethered embodiment), where all optical elements are conductively connected to the control and processing circuitry. The entire probe is quite flexible and adaptable to the shape of the forehead. This optical probe is held in place on the forehead by an elastic member (e.g., an elastic Velcro® strap. The second embodiment is wireless (i.e., untethered), wherein some or all of the optical elements are coupled to the control or processing circuitry using one or several transmitters and receivers. Thus, there are autonomous sources and detectors attached to the subject by means of a "band aid" or a tissue glue. The optical coupling does not require contact with skin so there my be a transparent membrane. The wireless coupling provides "freedom of placement" of the individual optical elements and untethered operation that makes the subject less aware of being optically examined (and thus promotes a more "real life" cognitive situation. This embodiment provides for a wireless, battery operated micro-sensor which will enable autonomous sources and detectors to be attached to the skin, coupled to each other by photon migration, as shown schematically in FIG. 2B. The micro-sensor may be based on nanotechnology thus providing small ("weightless") design.

Referring to FIGS. 2, 2A, and 2B, generally, optical probe 25 includes an LED source 102 and diode detectors 104, 106, 108, 110, 112, 114, 116, and 118. Source 102 is preferably a two or three wavelength LED. The individual detectors are preferably silicon diodes. Other suitable arrangement of sources and detectors is shown in U.S. Pat. No. 5,853,370, which is incorporated by reference In general, the optical probe includes two optical probes 25 and 25A, each having a light source surrounded by eight detectors. In the tethered embodiment, each photodetector is connected to one channel, as shown in FIG. 3. In the wireless embodiment, each photodetector preferably provides signal to a transmitter and there is a receives connected to the processing circuitry, as shown in FIG. 3.B.

Each light source 102 is driven by a driver 130 (shown in FIG. 4) constructed to receive a control signal from a timer 132, all of which are powered by a battery 134. Each diode detector 104 provides a signal to CMOS I-V amplifier 120, which in turn provides signal to a transmitter 124, all of which are powered by a battery 122.

Figure 2D:
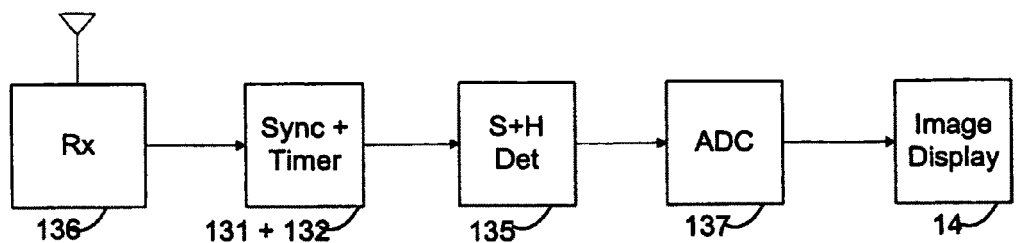
FIG. 2D shows schematically a receiver system used in the optical probe shown in FIGS. 2 and 2B.
Figure 2C:
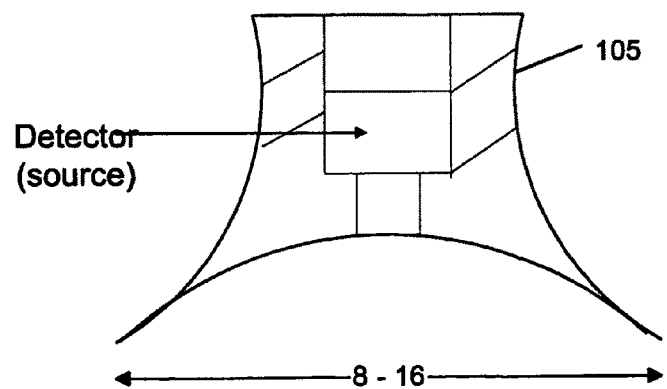
FIG. 2C is a cross-sectional view of a light source or detector element of the optical probe shown in FIG. 2A.

FIGS. 2 and 2A illustrate a preferred embodiment of the wearable optical probe including a mercury battery (122) for powering autonomous detector units 104 through 118 positionable on the forehead with no interconnection thereto. Each detection unit can be held in place on the prefrontal region by a strong double sided tape or a suction cup shown in FIG. 2C. A contact pad 101 provides a light barrier.

Referring still to FIG. 2A, there are eight parallel detector/amplifier/transmitter units, each including a silicon diode detector 104 connected to a C-MOS current to voltage amplifier 120 that provides pulse modulation to micro transmitter 124 and antenna all encapsulated and light enough to be held in place with double sided tape or suction cup, as mentioned above. The transmitter is sufficient for a 6 ft radio link in a crowded EMI atmosphere, as for example a pilot of an airplane. The LED illuminator 102 provides at least 2 wavelengths, time shared with a blank for dark current correction and for synchronization. A flip-flop timer 132 provides 4 pulses, 3 of which selectively activate 3 wavelengths for spectrophotometry, for example 720 nm, 805 nm and 850 nm. This timer illuminates the LEDs in sequence followed by a blank space as mentioned above which is used for synchronization and dark current correction. The average current of the LEDs is about 20 milliamperes and the voltage is about 6 volts, but 3 volt LEDs may also be used.

FIG. 2B shows schematically a wireless embodiment of an optical probe used with optical module 20. Probe 25 includes eight diode detectors each associated with a current to voltage IC, which in turn is associated with a cell phone FM transmitter. Each LED light source is associated with a timer (or clock C) and an LED driver.

FIG. 2D shows schematically a receiver system for a wireless optical module. A receiver 136 receives, for example, 8 pulse trains in sequence and knows what the timing sequences of the pulses are because of the blank space. Receiver 136 also knows which one of the 8 channels is communicating because they are frequency encoded. The blank signal activates a series of flip flops which mimic that of the LEDs and the gate 8 sample and hold circuits together with another set of switches that activate the conversion to an ADC for which 8 bits are sufficient. The receiver circuit includes a DSP for signal processing with a real time display of the signals within time and space so that a chronological trace as well as a spatial orientation is presented at 1 per second or shorter if desired since this is a parallel system and the acquisition time for each wavelength is 10 milliseconds times 8 detectors 0.08 sec.

FIG. 3 shows schematically a three-wavelength optical module designed for examination and imaging of cognitive functions. Optical probes 25 and 25A, located on the forehead of subject 8, collect optical data shown in FIG. 7. The system includes a gain control for calibrating the optical signal in μM, prior to brain examination, as described below. The optical data are provided to computed 12 in a digital format. FIG. 3A shows schematically another embodiment of the three-wavelength optical module that uses eight parallel channels for receiving optical data.

Referring to FIG. 3A, wireless brain imager 140 advantageously provides: (1) freedom of choice in source/detector geometry (2) freedom of movement for the subject (3) less bulky probe (4) isolation between the subject and the equipment, and (5) open field operation capability. This imager uses a probe having 8-channels, the input to each channel is obtained from one of the eight silicon diode detectors located around a single 3-wavelength LED source. It uses the frequencies in the ISM band to transfer the data from the probe to the remote receiver, where the data acquisition and analysis are done. The synchronization between the Transmitter and the Receiver is achieved using the Sync pulses, produced by the timing circuitry at the probe and transmitted every cycle.

In the system of FIG. 3A, everything is localized with a mercury battery timer and driver for the two or 3 wavelength LED (FIG. 2A) a mercury battery operated silicon diode CMOS detector and a radio transmitter using an RF frequency encoded system so that all 8 detectors are at a different transmitter frequency. Time multiplex is less complicated i.e., the only timer here is the light source that gives the 2 or 3 wavelengths and then a dark interval, which is used as a synchronizer. With local battery operation, each unit is attached separately to the brow presumably with strong double-sided tape and is termed a "Cognosensor". This gives the ultimate flexibility and a good measure of non-transmission from source to detector because each detector is recessed with the rubber rim around the edge of the light source.

In optical probe 25, the LED source is surrounded by a circle of silicon diode detectors with an equal separation of 2.5 cm. This is a suitable separation for obtaining optimal signals from the cortical layer of the brain and affords nearly equal background signals from all detectors.

For example, in order to exactly equalize the outputs from the 8 integrated chip silicon diode detectors, we interpose a fifty-dB digitally controlled gain stage. The output in the region of 1-5 V pulses at 5 ms time multiplex pulses are connected to a sample-and-hold circuit in order to obtain an averaged "peak value" over 100 ms. Here, simple reed switches are adequate to give closure during the peak value of the input signals at the three wavelengths as are provided by the computer clock-controlled time-sequenced switches. Instead of taking the output at the time of closure of the input switches, the averaged value is sampled by the ADC program at an interval when the charge on the capacitors has stabilized and an average value of over the preceding twenty (20) closures of the switch is obtained. Thus, ADC sampling can take place at any time except when the signal switches are activated to impart new information to the holding circuit. An 8-bit ADC is quite adequate and DSP signal processing thereafter is optimal in view of the excellent averaging properties of the sample-and-hold circuit. The back projection algorithm for imaging provides information for each one of the 16 sectors. (As an example, the circuit diagram of FIG. 4 is designed for 12 detector diodes.)

Referring to FIG. 3B, optical module 150 includes optical probe 25, also shown in F*ig*. 3A including a two wavelength light source 102 (LEDs $\lambda_1$ and $\lambda_2$) and eight light detectors $D_1, D_2, \ldots D_8$. In the optical module 150, the signal transmitted through the tissue and including the brain cortex is detected by the numerous silicon diode detectors, preferably 5.times.5 mm area to improve signal to noise ratio. The output is connected directly to a current to voltage converter with a 10-20 megaΩ feedback resistor for the 2.5 cm source detector separation. To adjust the signal output of the system to a standard value, a digitally controlled gain stage may be used. The output of the gain stage is integrated by a special sample and hold system. All channels are separately detected and the average peak signal value is accumulated in the storage capacitors (e.g., 0.1-0.01 microfarad). These storage capacitors require on the average 1 sec, i.e., 20 signal interations to reach 95% charge for each signal channel. These memorized signals are sampled periodically by the connection to the ADC (avoiding sampling when the signal level is being changed), so that only average values are involved. The output is displayed as an amplitude signal for values calculated at the three wavelengths to indicate oxygenation, blood volume changes in each of the 16 voxels.

Referring also to FIG. 2A, each cognosensor is "labeled" with its appropriate frequency also entered into a multi channel receiver for continuous clear reception from each one of the sensors. The wireless system may use different frequencies, for example, in the 433 MHz region, or for example in the 900 and 2400 MHz regions.

In the wireless embodiment, the cognotransmitter (i.e., the cogno-light source) drive a 2 or 3 wavelength LED at a sufficient light intensity level that can be detected by the cognosensor. For a 2 wavelength LED, the cognotransmitter consists of a multivibrator timing circuit, producing 'double pulses,' wherein the first of the double pulses excites the 730 nm LED and the second one the 850 nm LED. The timing circuitry provides a blank interval between the double pulses, which interval can be varied, effectively varying the duty ratio. The duty ratio can be set high during the active period, and low during the sleep mode. The high duty ratio can be used, when there is a necessity for a high signal to noise ratio and the battery drain is not paramount. This system is self synchronizing, where the data signal itself is utilized for synchronizing the Cognosensors and receiver circuitry.

After light detection, the signal level from the current-to-voltage converter is sufficient to modulate the transmitting system. The transmitter system delivers RF sufficient power to the receiver to be above background noise. Thus, the imager signal is bifurcated just after the current-to-voltage converter, which gives a signal level of about 1 Volt.

The entire wireless probe design focuses on minimum power dissipation and minimum weight, wherein the minimum weight enables attachment to the skin using adhesives rather than a Velcro strap. Thus, in this embodiment, each cognoscope utilizes a minimum of electronic function together with the above mentioned minimum power dissipation. For example, a 1 volt signal after the voltage to current converter can be achieved using a large detector (15 millimeter square) followed by a moderate sized resistor and a feedback circuit of the current to voltage converter 0.1 to 20 megohms depending upon the light intensity available.

Preferably, the cognosensor includes a large silicon diode, 16 $mm^2$ followed by the smallest available current-to-voltage chip and the available 430 MHz FM transmitter. This transmitter accepts an intermittent tone within its frequency range and a pulse duration of 3 millisec (i.e., 300 Hz.). For the two wavelengths, the system may use the "ON" interval from the cognosensor consisting of the 3 millisecond pulse and an "OFF" interval adjustable depending upon the "sleep" mode. Thus, the cognosensor transmits the optical information whenever it is received. The duty ratio is adjusted from approximately 1 to a very small fraction in the rest interval.

The Cognotransmitter has different design parameters. The first "off" it is electro-optically coupled to the sensor and thus it only sends a light pulse to be detected by the cognosensor. This is done by timer 132, LED driver 130 coupled to LED 102 and all powered by a power source 134, as shown in FIG. 2A. By using a nano ampere detector 104 of a large area, sensitivity is such that multi-wavelength LED 102 can be operated 20 mA giving the goal of six hour battery life time with a source-detector separation of 3 cm. The other item of the light source is a multivibrator or based pulse generator for the two (or three) wavelengths, and for an optional dark interval. These signals operate the LED and thus activate the cognosensor appropriately. The cognotransmitters send synchronizing information to the receiver and activate the LED light source. The system maintains a strict synchrony of the receiver and the light signals transmitted from the cognosensor. The receiver has no requirements for miniaturization. Alternatively FM reception at 430 or 930 MHz can be operated at the 0.15 μV level with a commercial FM receiver.

The synchronization between the cognosensors and the receivers is obtained from the data itself, making it a self synchronizing system. The system may have a selected number of channels, for example, four or five channels might suffice instead of eight channels (one per cognosensor). The FM receiver output is connected to a digitally controlled amplifier and sample and hold and ADC connection just as in the basic non-telemetered system, shown in FIGS. 3 and 3A.

The data processing was performed as follows: The data for a particular set of anagram questions in a particular voxel are accumulated to form a histogram display of intensity signal [micromolar hemoglobin increment over baseline] times the number of observations of that value of signal, usually scaled every 0.1 µM and with several hundred entries to the histogram. These histograms are formed for each one of the 16 or 18 voxels and are displayed on a chart. On that chart the fiducial marks indicate the change from one level of anagram difficulty to another. The raw data at the 3 wavelengths is processed so as to afford oxygenation [the difference of absorbance at 720 nm and 850 nm is converted to oxygenation change and to blood volume change by the concentration weighted sum of absorbance at 720 nm and 850 nm. These charts are then computer analyzed and digitized and an average value is obtained for each level of difficulty [in contrast to the time-resolved data acquisition where each image of the values is stored every second for voxel]. Crosstalk between oxygenation and blood volume is minimized by appropriate testing with blood models.

The data display is as follows: Values for each letter anagram are accumulated from the 8-week interval of study to afford for each voxel approximately 400 data points from which the scores are computed. Instead of using a customary back protection image for a data display, we prefer a display of the experimental data as follows. The histogram program calculates the maximum value in incremental micromolar concentration as mentioned above, usually with respect to the initial 3-letter anagram. Each histogram is fitted to a Gaussian curve which is inspected for obvious outliers (>2×sd) and bimodal distributions are manually selected, that is, the signature voxels are selected. Thus, data display takes the most probable incremental value and identifies its probability as follows.

The resolution is indicated in this contribution by the singularity of the voxels, i.e. if no resolution were available, then indeed the field would be of uniform intensity, all values being of similar probability. The incremental values would be of similar probability and "chaotic fields" would be obtained. If on the other hand some voxels are truly dominant, then indeed the discretization of the voxels would be observed as is the case in students responding under conditions where fruitful outputs are obtained, i.e. a high frequency of "hits" or solutions is observed together with activation in a few voxels.

Figure 10A:
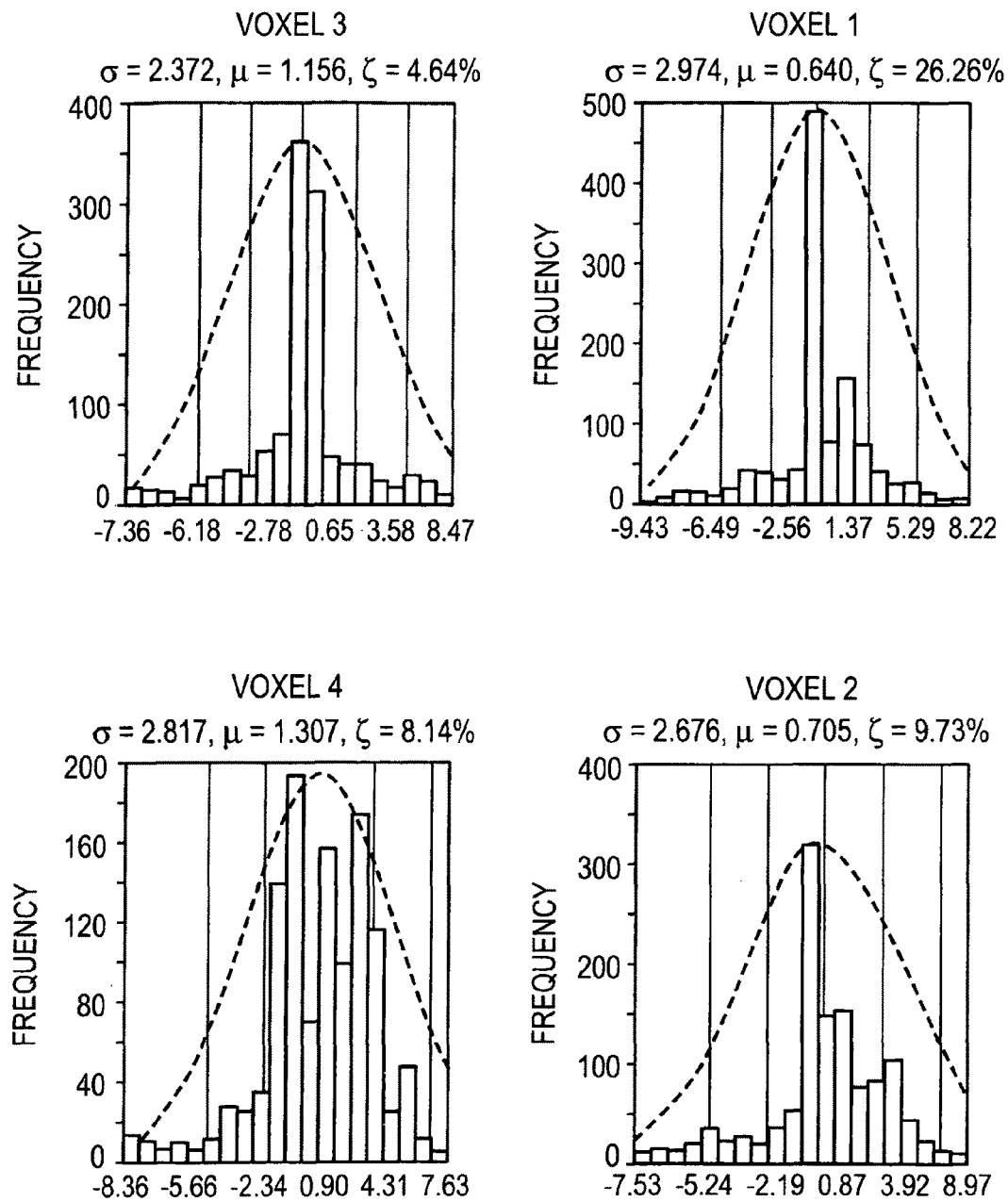
Figure 10B:
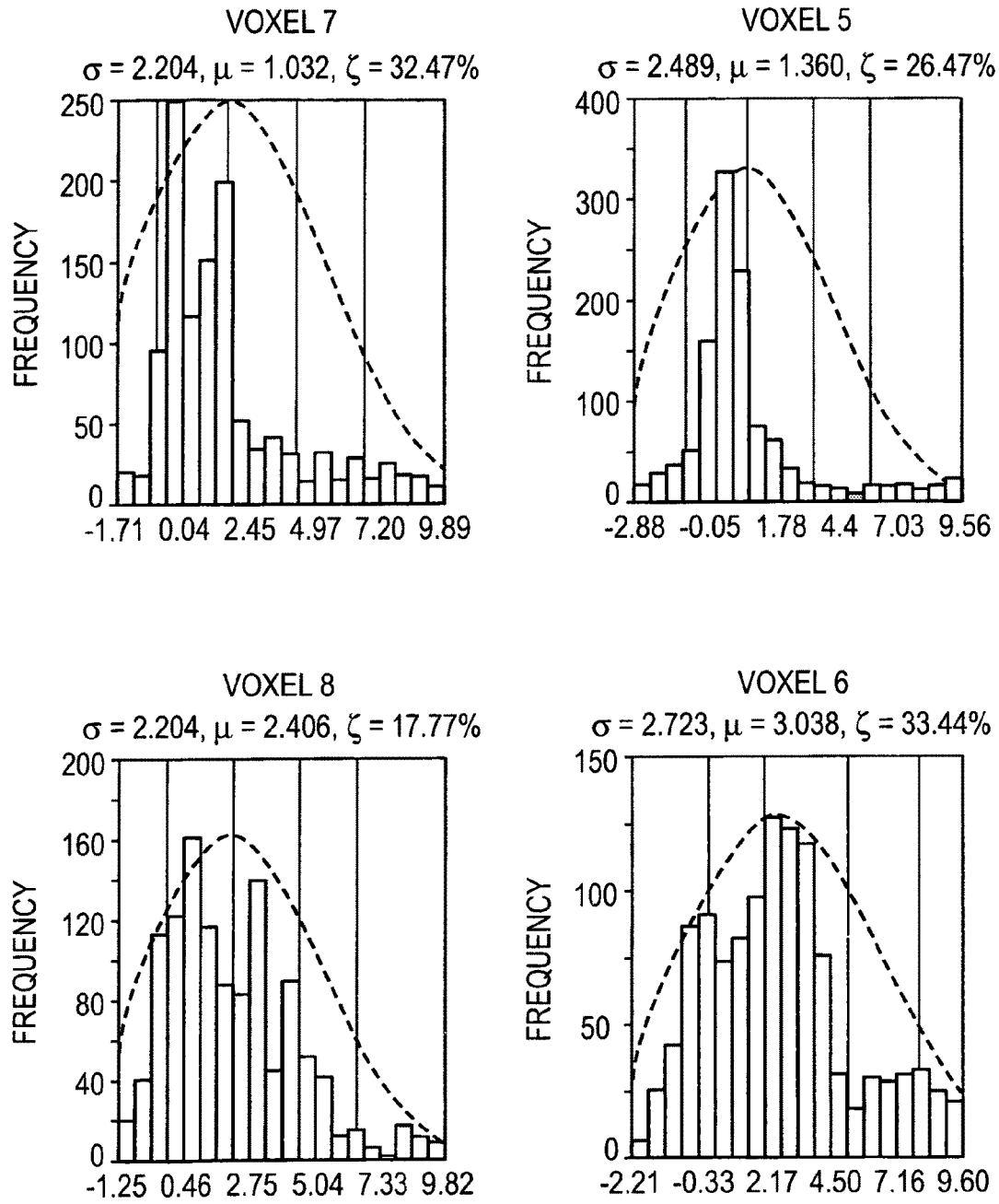
Figure 10D:
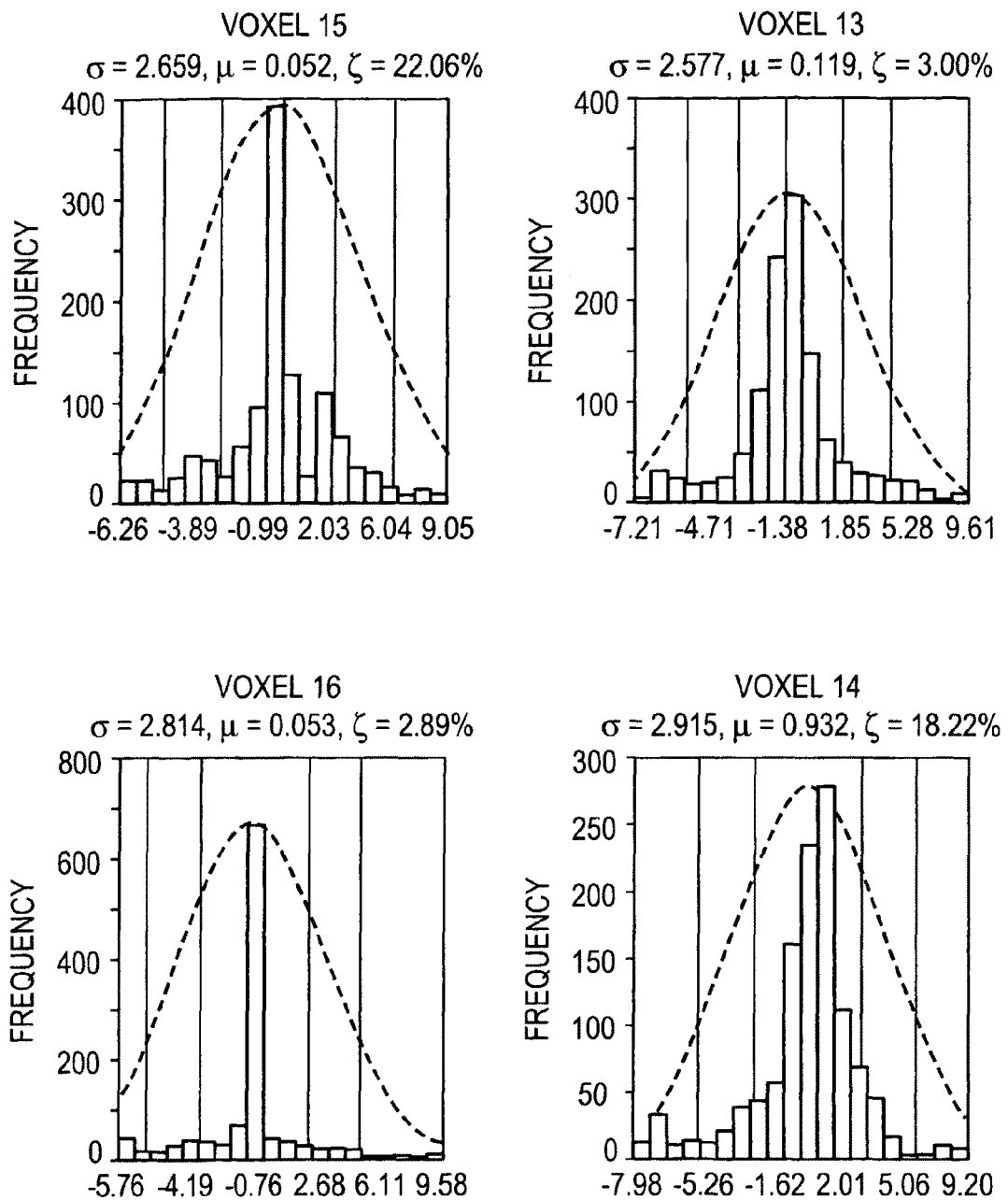

Instead of imaging the back projection average of intensities between the pair of sources and detectors (as done in U.S. Pat. No. 5,853,370, central computer takes the output from a single detector and provides a statistically significant average of the experimental data (as shown by the histograms provided in FIGS. 10 and 12) This data consist of an intensity reading.

The population on which the data have been obtained is composed of high school students from neighboring schools in the Philadelphia area. In all cases IRB approved informed consent was obtained from the subject or from the parent in the case of the minority students (University of Pennsylvania) and from the mother in the neonate studies and records are kept on file. Several hundred studies have been made under these protocols with no untoward effect.

Figure 9:
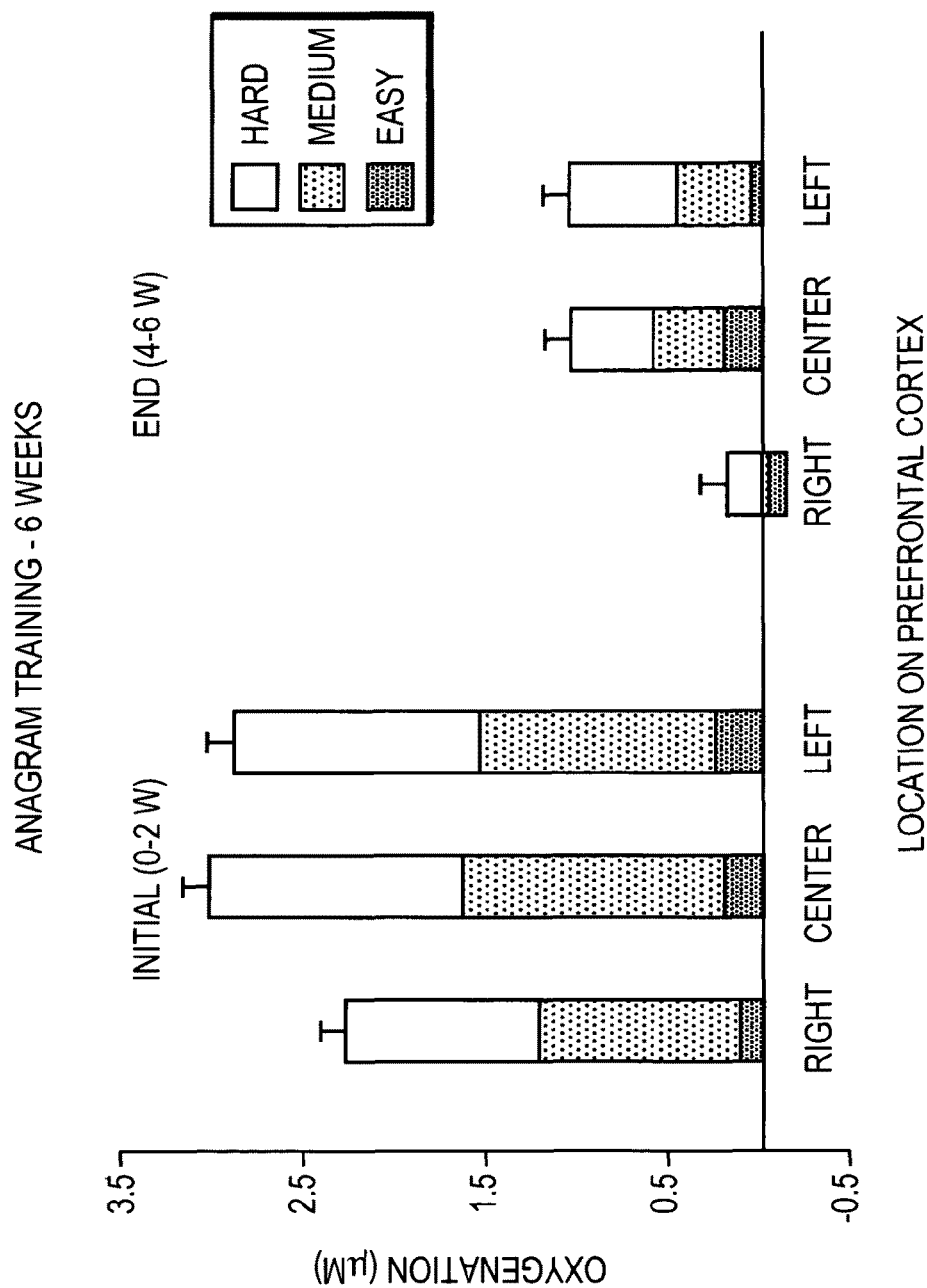
FIG. 9 shows graphically an oxygenation signal, collected by the brain examination and imaging system of FIG. 1, for the right, center, and left of the prefrontal cortex initially and after a training period for solving anagrams of different length.

The subjects get a series of lectures and they start studying their brain function with anagrams and they get a lot better over time. Each person was solving 3, 4, 5 or more letter anagrams. Three letter anagrams are for example, "the" "eht", etc. Initially, each subject was trained for 6 weeks, the results of which are shown in FIG. 9. After two weeks, they become expert. Five letter anagrams are reasonably difficult, and the corresponding signature of the brain is completely different.

Figure 7A:
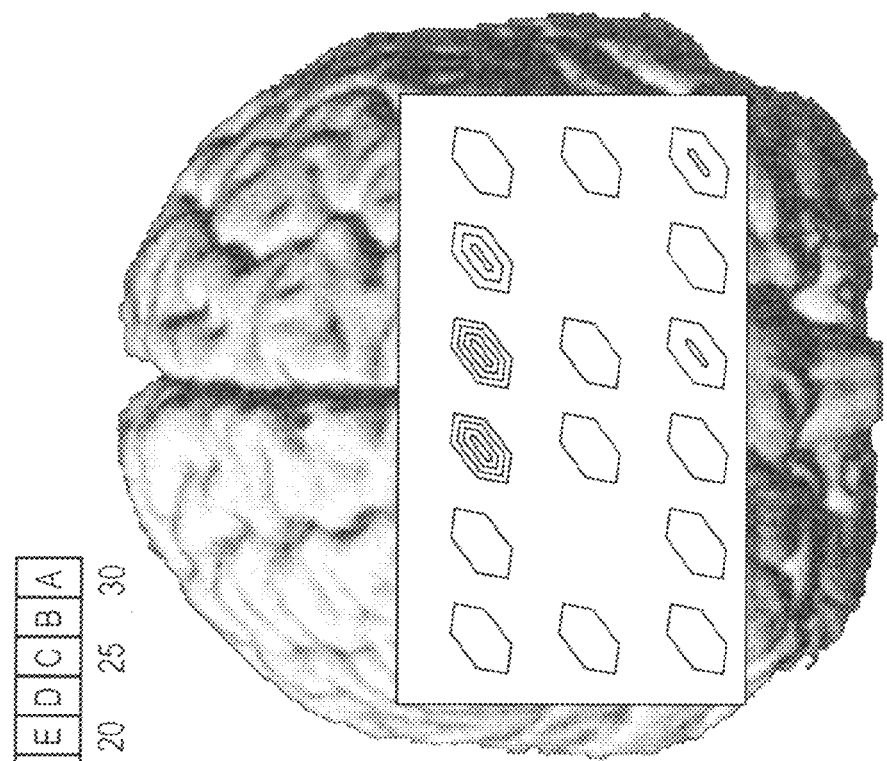
FIGS. 7 and 7A show optical images, generated by the brain examination and imaging system of FIG. 1, initially and after a training period.
Figure 7:
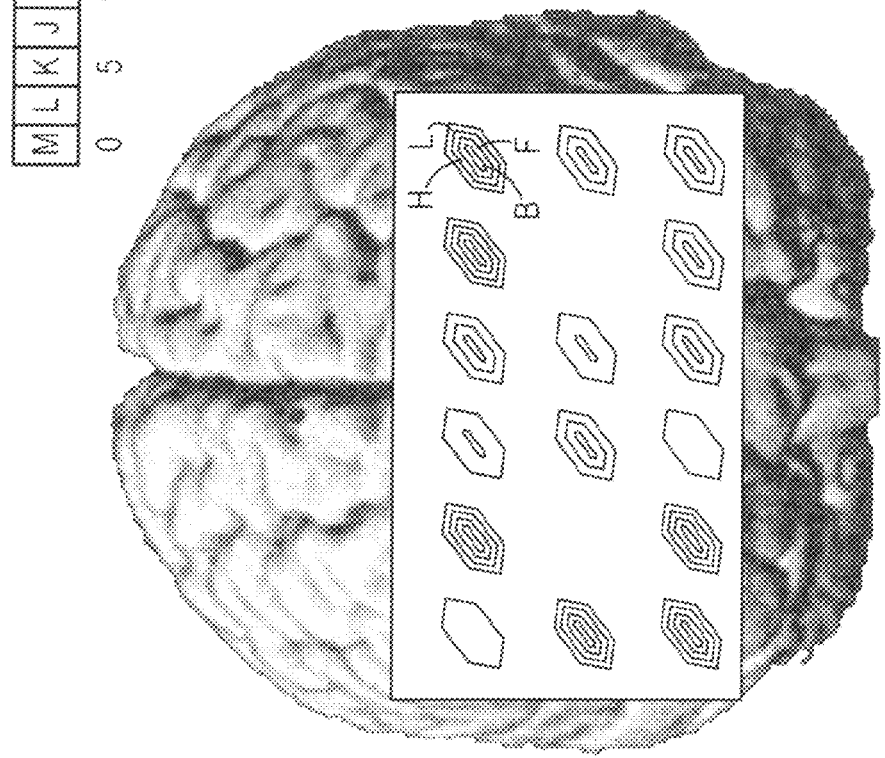
Figures 7B, 7C:
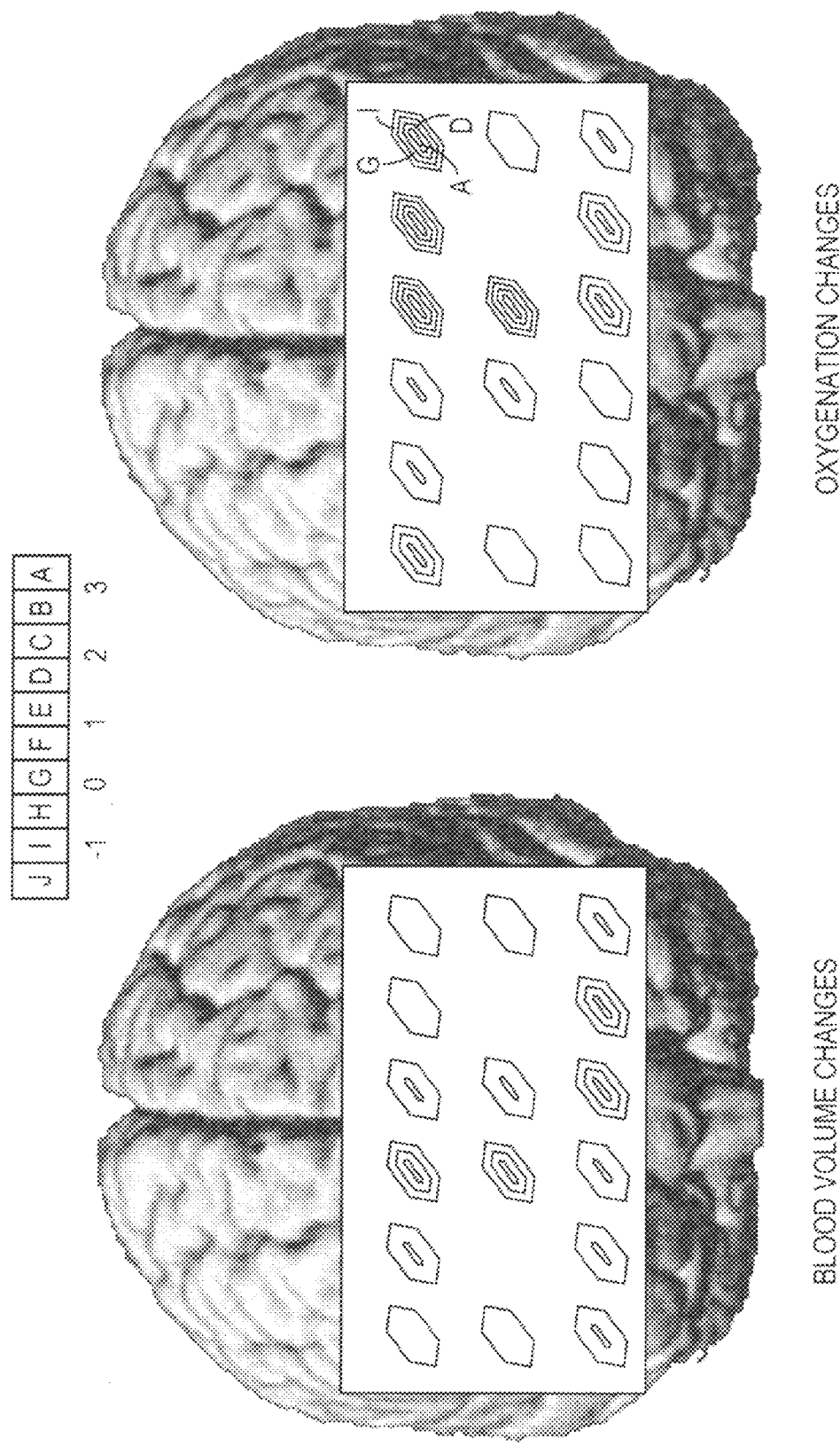
FIGS. 7B and 7C show optical images corresponding to blood volume changes and oxygenation changes when solving 8 letter anagrams.
Figure 7D:
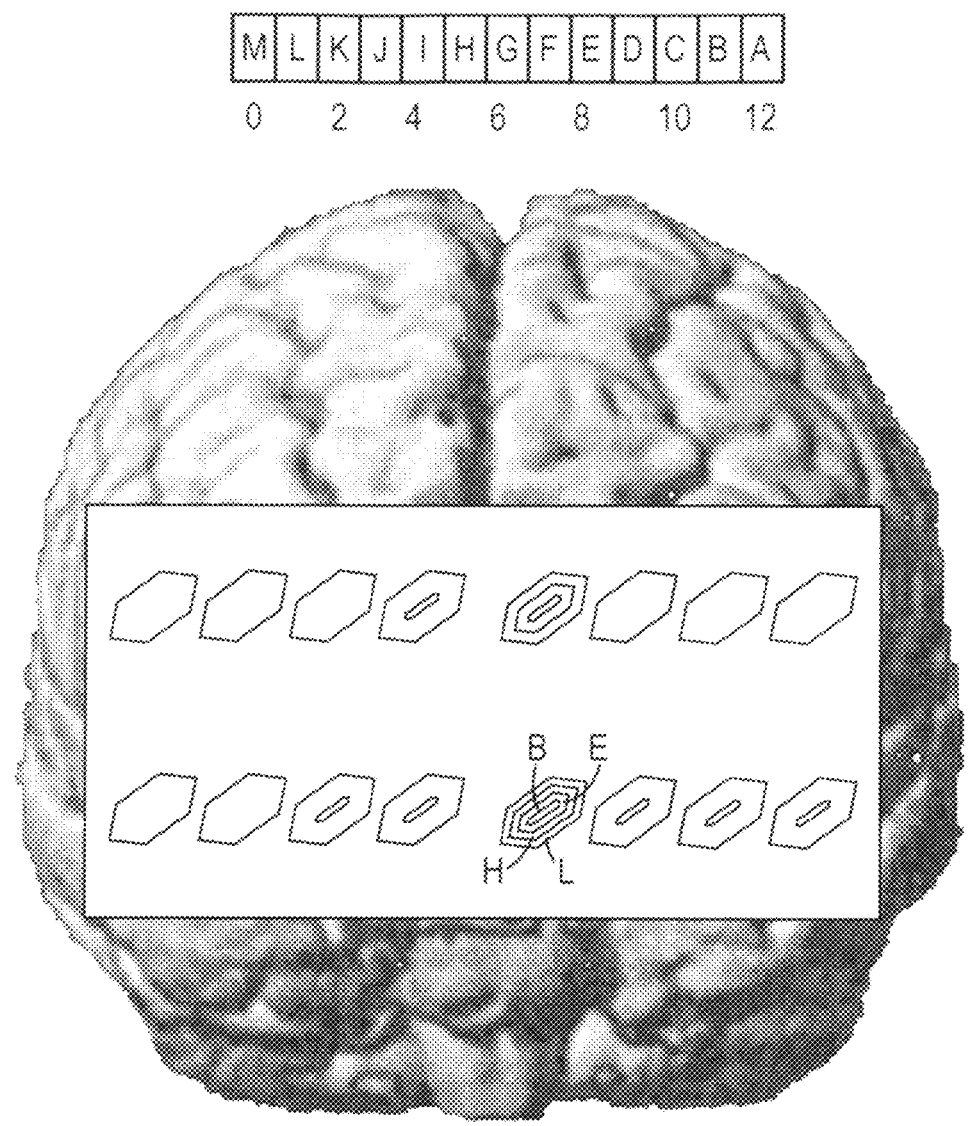
FIG. 7D shows a sudden insight optical image for oxygenation changes 15 seconds after solving an anagram minus 15 seconds before solving the anagram.

FIGS. 7 and 7A show optical images, generated by the brain examination and imaging system of FIG. 1, for solving 5-letter anagrams initially and after a training period of several weeks. As shown in FIG. 7A, after several weeks, the hemoglobin oxygenation signal is more localized, and the overall oxygenation signal is reduced with the increasing number of solutions. The "images" are collected during the brain activation and formed using the standard RADON back-projection algorithm used in X-ray imaging. Then, the data is weighted to show the frequency of occurrence of the detected optical signal as a percentage of the total detected signal for the signal intensity relative to a standard.

For a subject who had learned Chinese (and wasn't very good at English) several hundred observations of 3-letter anagrams were focused in just a single voxel (i.e., the signature voxel), but with four letter anagrams the solution rate went from 250 to 50. At this point the dominant signature voxel disappeared and the optical signal became smeared. In other words she couldn't focus, couldn't match between difficulty and ability. The subject was frustrated by having a problem too difficult that corresponds to a "smeared" optical signal over a number of voxels.

In general, the present studies display optical data as histograms of the total number of observations obtained for that particular individual over the several weeks of data accumulation, either before or after a three-week interval of training. The pre-training data will represent a progression of improvement averaged over the three weeks.

In order to give an effective score of the data of the performance of a single individual, over the six weeks of observation, I have arbitrarily divided the results into two categories termed pre-, training, and post-training. Spot observations suggested that training in anagram solutions seem to be achieved in a two-to three-week interval, beyond which the score was highly consistent for the difficulty/ability match. Taking note that fresh sets of anagrams were used in each test so that memorization was not a factor in the pre-and post-training interval. (NB: Optical detection at a depth of about 1.5 to 3 cm have been demonstrated and co-registered with NMR signals. Both in vitro and in vivo validation were performed).

In summary, the optical probe of FIGS. 2, 2A and 2B was used to measure functional responses in a particular place on the forebrain. The enclosed graphs (shown in FIGS. 10 and 12) display several hundred observations where the magnitude of the signal is plotted for the corresponding voxel.

FIG. 9 shows a typical result showing the effect of training. The subjects start studying their brain function with anagrams and they get a lot better over time. After two weeks, they become expert. As soon as those connections are made, after a couple of weeks the optical data exhibits a well-defined signature voxel. This is an earmark of the functional brain, that it uses just a couple of small parts of the prefrontal region that is about 4 mm thick.

The optical results show a motivation factor. When the subject is highly motivated the brain optical signature changes. Initially a subject was solving three letter anagrams but after several sessions the signature voxels became less pronounced. Then the subject was solving eight letter anagrams he churned almost twice as many and the optical data show that he used just two focal points on his forebrain while here it was weak signals everywhere, the scale was over here, and unfocused. The optical data show that when the brain is working, it concentrates its energy on the places, the neural net, which can solve the problem. We can identify that, and that is what's new about this, we can measure when the brain is solving the problem optimally.

The scoring is affected by vocabulary limitations particularly in those for whom English was a second language. Thus, a two-to three-week interval of practice in solving anagrams was instituted using different anagram lists in the various tasks so that memorization was not a factor. Thus, the results from the first three weeks were termed pre-training whilst the results after two to three weeks were termed post-training. Under these conditions, the match between difficulty and ability either shifted towards higher difficulty or the number of solutions obtained was greatly increased.

Usually, brain study data display the intensity of the signal as computed from back projection for available source detectors. In this case, the emphasis was on the validity of the data rather than exact location of the voxel. The criteria are:

1. the intensity—usually in micromolar concentration for both oxygenation and blood concentration.
2. a histogram is created displaying all the values for the three weeks interval. The histogram is studied in detail to eliminate obvious outliers by formula those values, which are two times the standard deviation of the Gaussian fit to the data.
3. By inspection values which not only fit that category but values for which there are no more than five observations. Thereafter, a new Gaussian fit is made to the data and the FWHM (Full Width at Half Maximum) characteristically of the data display for Full Width Half Maximum is computed from the computed fit to the outlier free data.
4. Finally some measure of the number of observations is included in two ways. One, the number of observations is at the most probable concentration change or the number of observations under the Gaussian fit. We prefer the former, although except that the data can be analyzed by the latter. We term these values to be "Figures of Merit" for the particular series of tests.

The display of the data is simply the figure of merit calculated for each one of the 16 detector positions, taking note that this is not the correct position as indicated by a back projection algorithm, but nevertheless, it is simple and direct. The goal of data display is to show:

a) where is the most "fruitful" or signature voxel; and
b) what is the significance of that voxel compared to other voxels in the display or other studies.

The data display has merit, i.e., fits the Gaussian curve, and that a significant number of observations were detailed. In order to indicate the statistical significance of the data without separate displays of signal size and standard deviation we have chosen a different representation particularly in order to decide which voxel is predominant.

The goal of the data display is to determine whether some source/detector combinations are more fruitful in giving margins of consistent signals than others. Instead of an intensity display as is the usual case with MRI, the above-described system displays the statistical significance, of not only of the intensity of the signal, but also its statistical significance. The former is displayed simply by the concentration change in micromolar units with respect to some standard (see below) the statistical significance is displayed by the FWHM of a Gaussian fit to the data from which outliers have been removed. Statistical significance is further indicated by the number of observations. Thus, the signal intensity is equal to $\mu c \cdot n/f$, where c is the incremental concentration and f is the half-width of the Gaussian fit to the data of outliers removed and n is the number of observations in the maximal reading.

The system performs a baseline correction. Since the images are incremental values with respect to a baseline, special attention has been paid to securing a reliable baseline value. The baseline has been taken before and after the test. In the more difficult anagrams it has been found that there is a general background incremental response, but nevertheless, the data baseline is taken.

The goal of the data display is to indicate the magnitude of the signal in:

(1) one of the 16 voxels studied (using optical probe 25);
(2) the reproducibility of the signal in terms of the FWHM of the Gaussian fit to the outlier corrected histogram for that particular voxel;
(3) provide an indication of the number of observations acquired at that particular voxel. For optimal results, the signal amplitude should be maximal, the FWHM should be minimal and the number of observations should be maximal.

In order to represent not only the presence of a signal in the forebrain image, but also to indicate its statistical significance, we create in each voxel the following quantities; the intensity of the signal (incremental hemoglobin concentration, micro Molar), multiplied by the number of times this particular signal is observed (see histogram display), divided by the FWHM of the histogram which has been corrected for outlyers (generally, outliers consist of less than five observations, and signals that are over two times the standard deviation). The histogram correction is done generally by inspection, particularly to determine if the histograms are bimodal which is often the case. Here again, the separation between two histograms would be in terms of the frequency of the occurrence dropping those measures of less than 5 observations with an amplitude which is less than two times the standard deviation.

The increased productivity and focal localization of responses following two weeks of training in solving anagrams in pre-two weeks of training as compared with post-two weeks of training in solving five letter anagrams. In the training period, none of the 18 voxels stands out clearly as dominating the response field as if the subject trying different ways to solve the anagrams in different portions of the forebrain. 326 solutions were obtained in the pre-training study with five letter anagrams. In the second two-week training interval, nearly double the number of solutions was obtained in the corresponding time interval, and the responses were localized in two principle ("fruitful") voxels symmetrically located with respect to the sulcuis. Nearly all other voxels were inactive except for three very minor peaks down by a factor between 2 and 10 with respect to the principal voxels.

Figure 11:
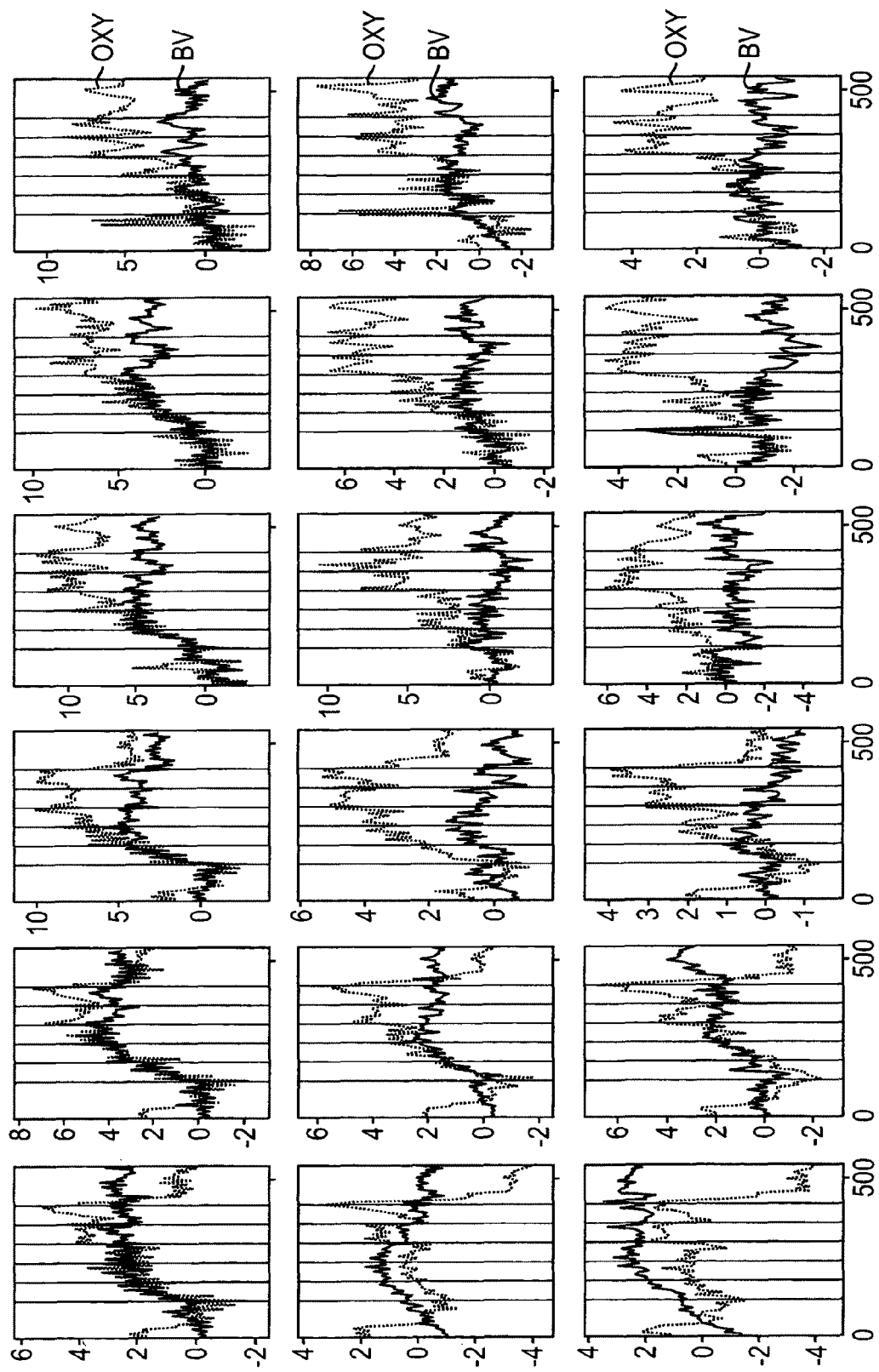
FIG. 11 shows the blood volume and oxygenation signals plotted for separate voxel over time.

FIG. 11 provides a comparison of oxygenation (OXY) and blood volume (BV) signals for 500 sec. Strong and prominent signals are obtained for oxygenation change consistent localized responses shown in FIG. 11. There are smaller responses to blood volume change (shown in FIG. 12 by different scales).

In summary, when there is a match between difficulty and ability, the oxygenation changes appear to be dominated by one or two voxels; one of which at least is on the mid line and often both are symmetrically located with respect to the midline as if there was a special signal in the midline sulcuis. The reason for this may be that the sulcis presenting a larger optical thickness of cortex that might give better signal. The predominance of these signals is clear as is their usefulness in identifying prefrontal responses.

1. The optical results provide consistent observation of oxygenation as the principal prefrontal response to functional activity. The results appear to support reproducibility of the approach, the half-width of the histogram in the voxels in which matches between difficulty and ability is achieved. Reproducible data from human subjects over 3-4 weeks of testing can be obtained with a FWHM or R^2 for the functional fruitful voxel across a limited population of students. However, there is no transferability between subjects; that is, the location of the signature voxel varies between subjects,
2. Disattention and frustration in problem solving results in chaotic optical responses in which none of the sixteen voxels clearly predominates.
3. In all individuals tested, when a match between difficulty and ability is achieved, one or two voxels predominate and provide reproducilibty in signal intensity. Notably, a higher signal-to-noise ratio will be obtained when the data just prior to and just following the solution of the anagram is recorded, the subject of further research.

Figure 5:
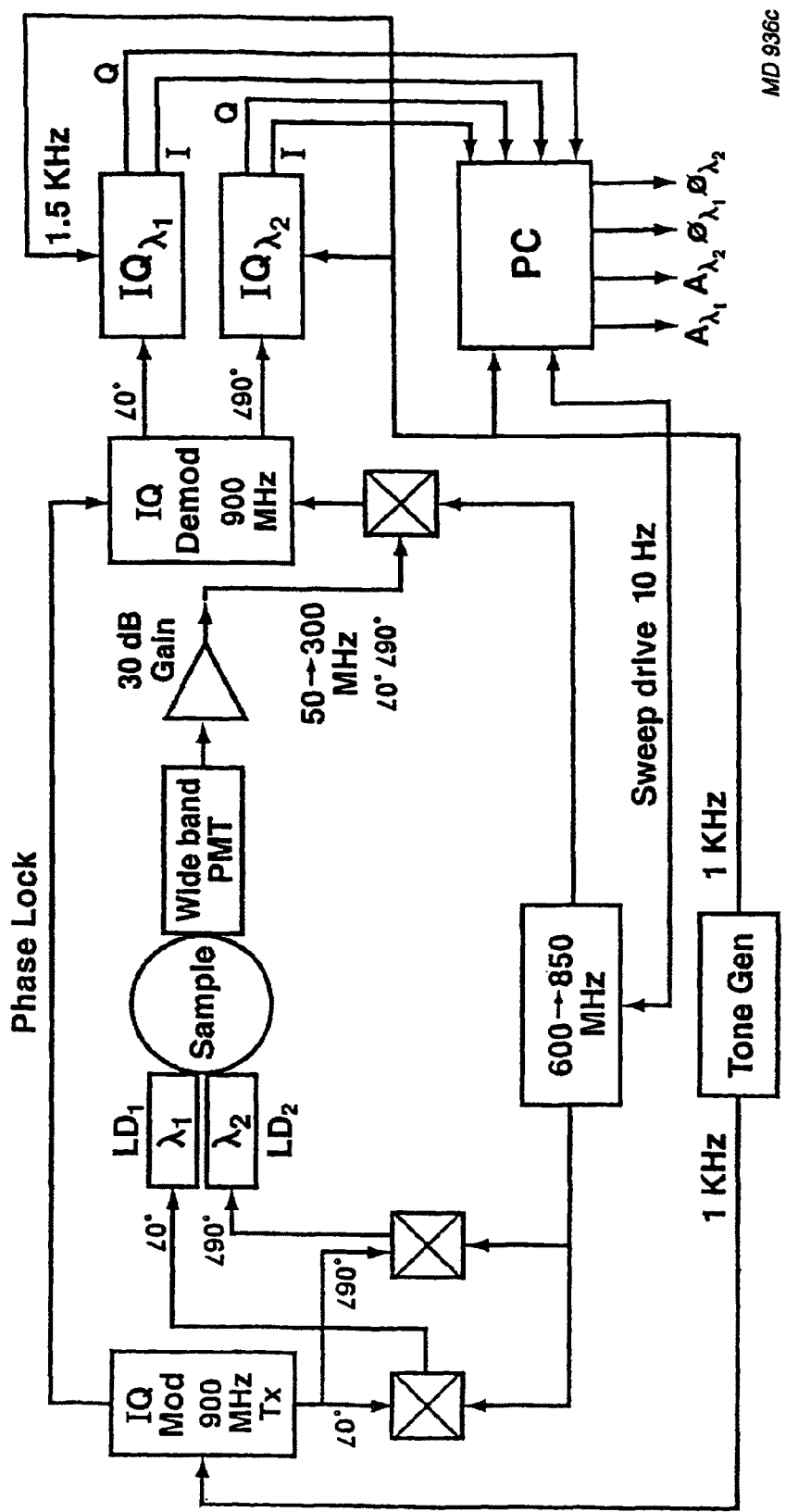
FIG. 5 shows schematically an IQ optical module for brain examination or imaging.
Figure 6:
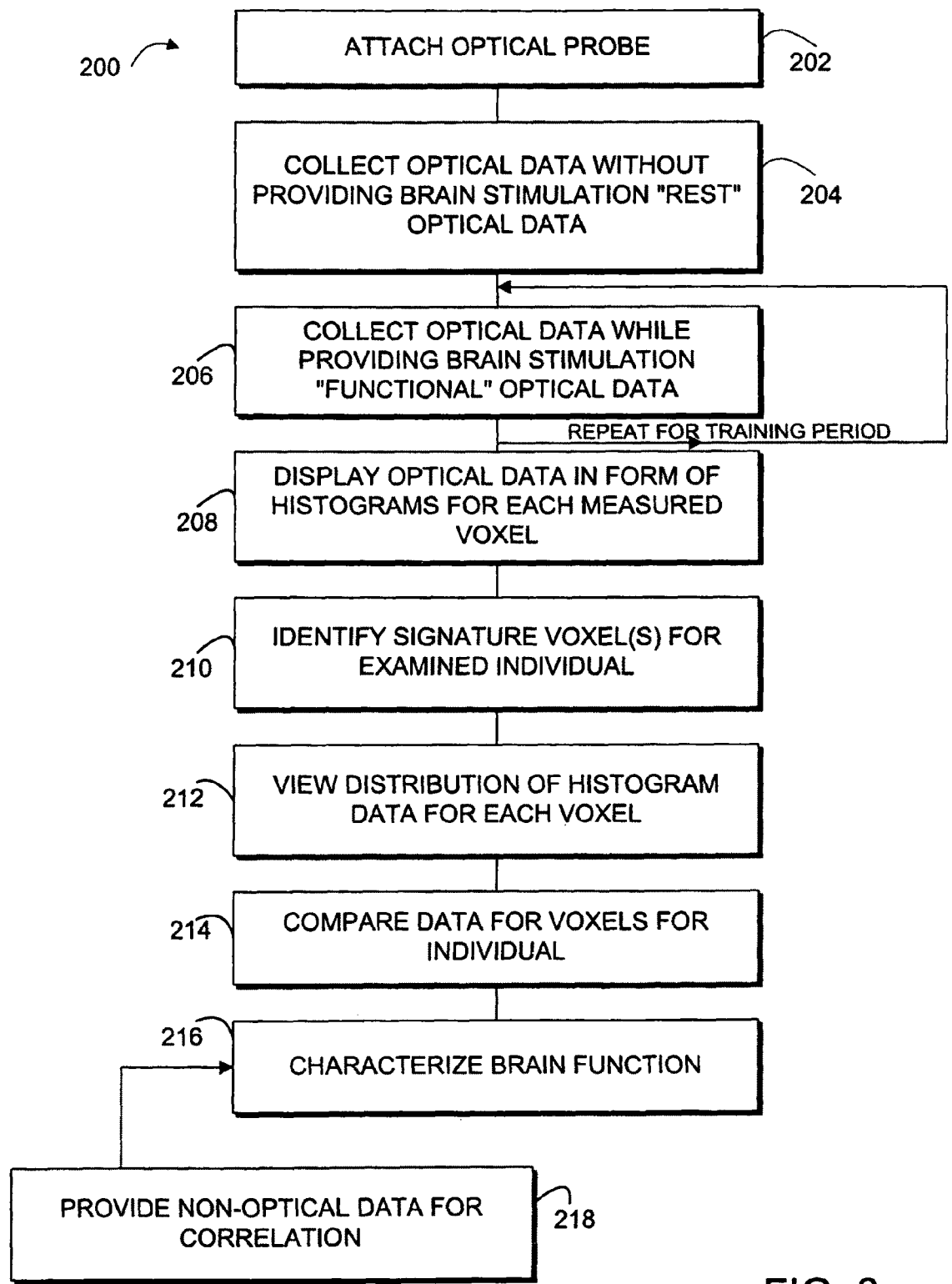
FIGS. 6 and 6A are flow diagrams of a process for functional brain examination using the brain examination and imaging system of FIG. 1.
Figure 6A:
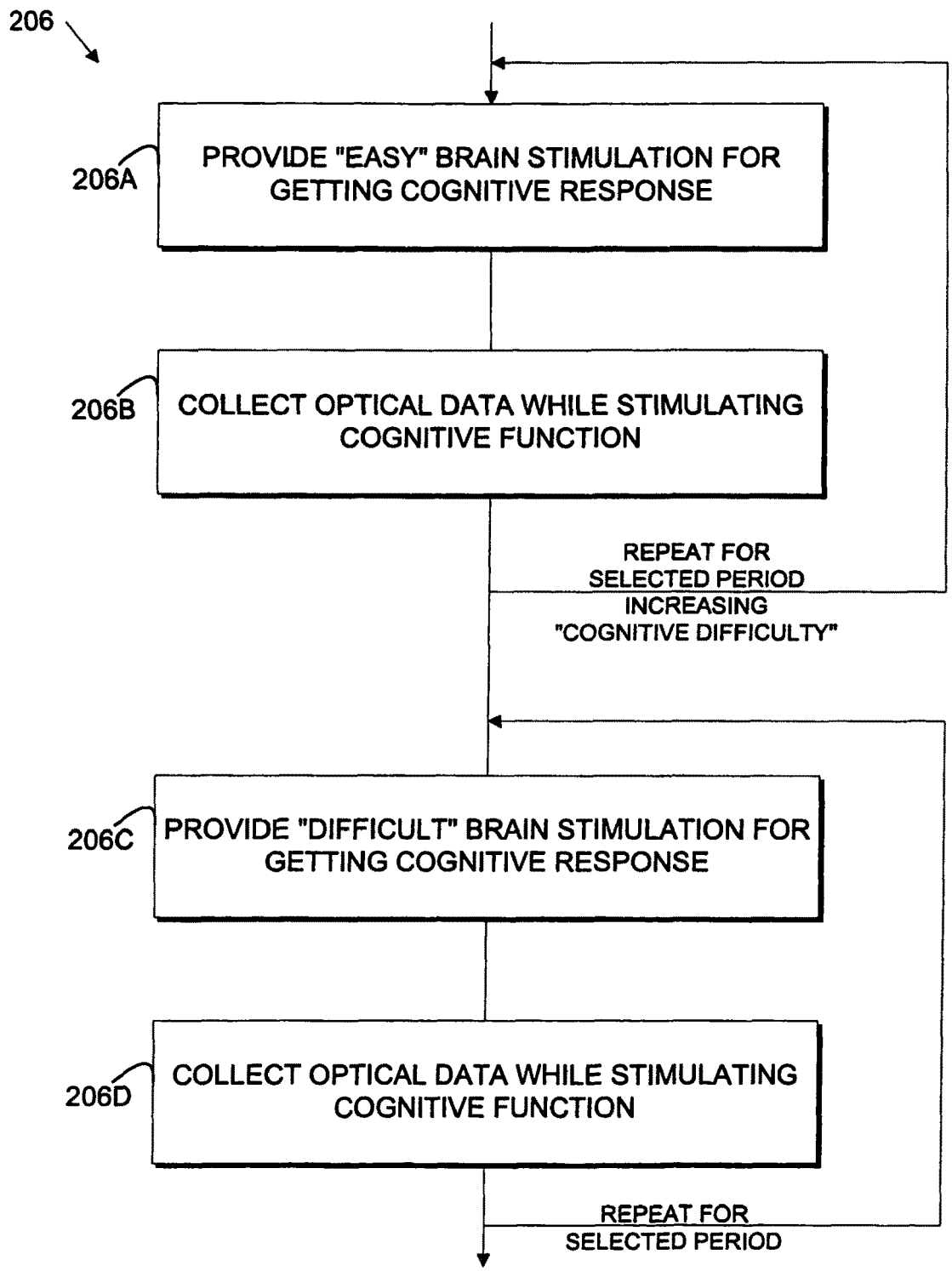

FIG. 5 shows schematically an IQ optical module for brain examination or imaging. This IQ optical imaging system is described in detail in U.S. Pat. No. 5,553,614 or PCT Application PCT/US99/03030, both of which are incorporated by reference.

All subjects have shown reproducible responses to problem solving giving sharply delineated voxels when difficulty and ability match. The subjects provided chaotic patterns for disattention and frustration, where signature voxels were significantly diminished or completely disappeared when compared with other voxels. The sensitivity of this imagery to perturbations demonstrates that the above-described optical systems can be used to detect emotional stress, fatigue, etc. This is important for operation of machinery, aircraft or other attention sensitive systems.

FIGS. 10, 10A, 10B and 10C show optical data plotted in form of histograms for individual voxels corresponding to brain regions in the prefrontal area. The histograms correspond to the magnitude of the oxygenation signal collected during the process of solving 6 letters anagram by a single individual. Each histogram is a plot frequency of occurrence for detected optical signal intensity. As shown in FIGS. 10A, 10B, 10C and 10D, voxels 1, 2, 15 and 16 provide a sharply defined signal and have a relatively small FWHM. These voxels can be designated as signature (or fruitful) voxels.

FIG. 11 shows the blood volume (BV) and hemoglobin oxygenation (OXY) signals plotted for each voxel over time. These traces indicate that the metabolic stress occurs in the "precognitive" interval and a deoxygenation occurs about 10-15 seconds before the sudden insight moment (i.e., the "cognitive" key press at the moment of solution) The relaxation phase of diminished metabolism and thus hyperoxygenation (high oxygenation signal) occurs together with a blood volume signal increase corresponding to a "luxury" perfusion.

FIG. 12 shows histograms for the blood volume and oxygenation signals of FIG. 11 plotted for two selected voxels 2 and 8 collected while solving 5-letter anagrams and 8-letter anagrams. The 5-letter optical data suggest sharper concentration of brain activity on a more localized brain region. Due to the difficulty of 8-letter anagrams, the subject "loose concentration".

Figure 3C:
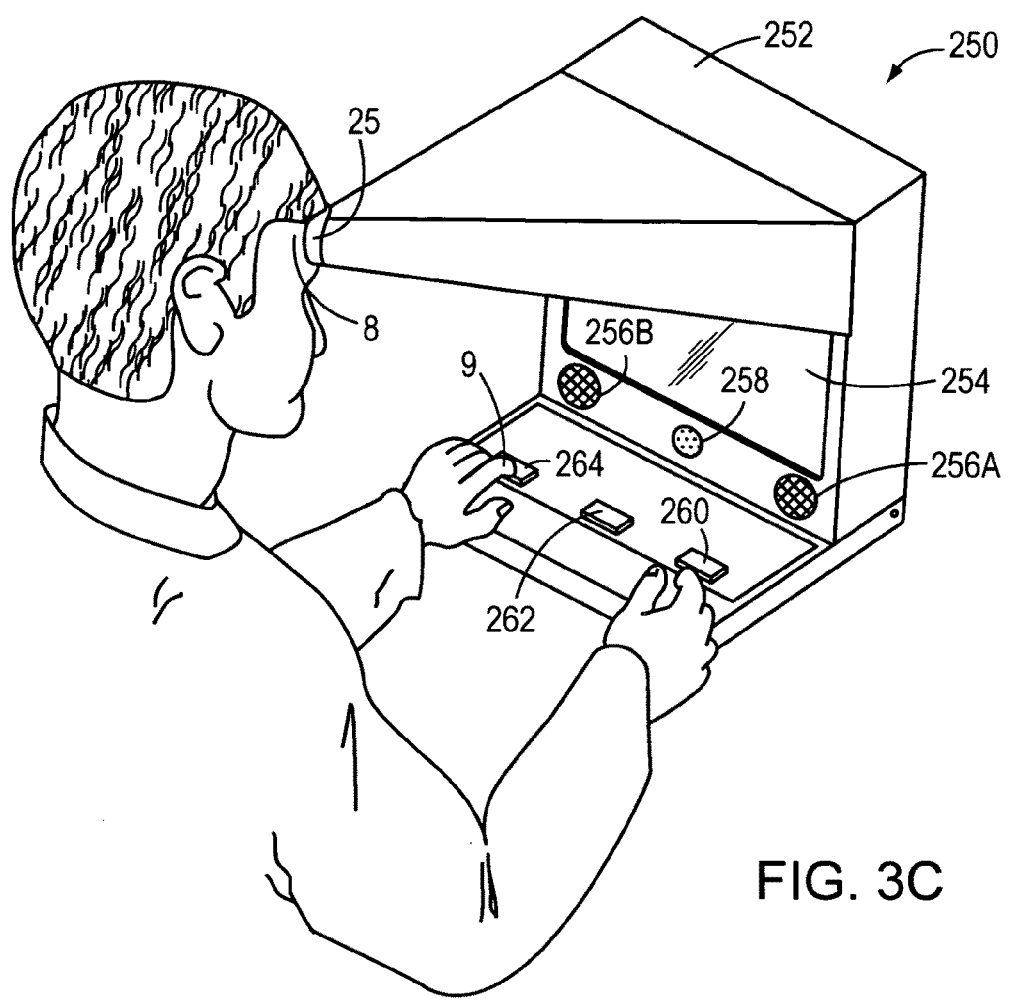
FIG. 3C show an embodiment of the optical deceit detector unit that uses any one of the systems shown in FIG. 3, 3A, 3B or 5.

FIG. 3C shows schematically a preferred embodiment of a deceit detector unit that can be used at an airport, a border entry point, an entrance to a campus or building, or another location, where potential threat from an individual has to be determined. Deceit detector unit 250 uses preferably the optical detector shown in FIG. 3, 3A or 3B for determining a "deceit" level by an individual. Generally, a deceit detector may use also other units shown in FIGS. 1A and 1B.

Deceit detector unit 250 includes a detector arm 252 for locating optical probe 25 (shown in FIG. 2) in front of the unit in a manner that is "accessible" by the forehead of an individual being examined. Deceit detector unit 250 also includes a video screen 254, speakers 256A and 256B, a microphone 258, and a set of input buttons 260, 262 and 264 providing a user input-output interface. Video screen 254, and speakers 256A and 256B belong to the brain stimulation module 30, shown in FIGS. 1, 1A, and 1B. Before or after brain stimulation, the user's responses are received using microphone 258 or input buttons 260, 262 and 264.

Figure 13:
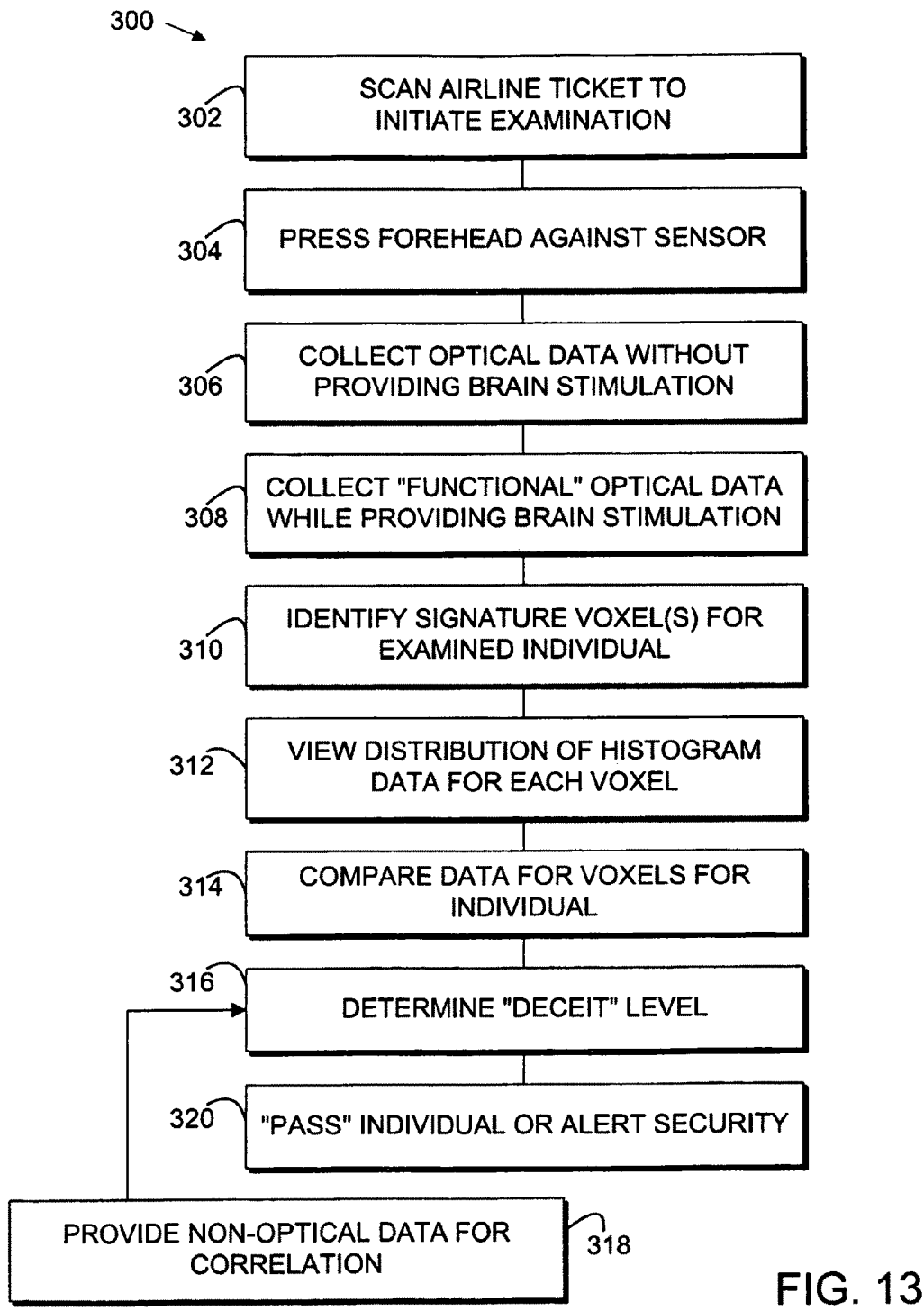
FIG. 13 is flow diagram of a "deceit" examination process used by the deceit detector unit shown in FIG. 1.

Also referring to FIG. 13, deceit detector unit 250 may be used in an airport terminal during the passenger check-in. An individual, waiting in the check-in line, will come to a stand-alone type unit and insert his or her airline ticket into a scanner (not shown in FIG. 3C). The scanner scans the airline ticket to initiate examination (step 302). Based on the scanned airline ticket, a computer retrieves from the memory any available data about the individual being examined. Video screen 254 provides instructions to the individual to press the forehead 8 against sensor 25 (step 304). This instruction may be provided in several languages or graphically in an easily understandable manner. These instructions may also be provided via speakers 256A and 256B so that deceit unit 250 can operate without an attendant. Optical probe 25 is designed from a pliable material providing good optical coupling of all sources and detectors to the foreheads of various shapes and sizes of different individuals. (There may be separate units designated for children, and for male or female passengers.)

After the examined individual presses his or her forehead 8 against optical probe 25 an initial pulse, oxygenation and blood volume scan is performed to verify proper optical coupling. Then, deceit detection unit 250 collects "background" optical data without providing any brain stimulation (step 306). Thereafter, deceit detection unit 250 provides brain stimulation using video display 256 and speakers 256A and 256B (step 308). During the optical examination, deceit detection unit 250 receives user input via a microphone 258, or input buttons 260, 262 or 264. While providing brain stimulation and receiving cognitive response, optical probe 25 collects "functional" optical data (step 308).

Deceit detection unit 250 is programmed to provide brain stimulation of varying degree. Initially, the examined individual is asked simple, common sense questions for which the truth or false is easily determined. Gradually, deceit detection unit 250 can increase the difficulty level of the asked questions. The examined individual may be asked to solve simple or difficult mathematical problems, or solve anagrams of varying difficulty (i.e., the number of letters), to obtain a basic image of the user's brain. Thereafter, deceit detection unit 250 gives the examined individual questions related to "threat level". The questions may include, for example: "Did you pack your luggage?" Did you give your luggage to anybody else for any period of time?" "Do you have a knife in your luggage?" "Do you carry a weapon?" Deceit detection unit 250 collects optical images while the examined individual is asked "threat" questions and provides the corresponding responses.

Optical detection unit 250 can collect separate blood volume and blood oxygenation images as described in U.S. Provisional Application 60/438,229 filed on Jan. 4, 2003, which is incorporated by reference. Deceit detection unit 250 then identifies one or several signature voxels for the examined individual (step 310). Next, deceit detection unit 250 identifies and views the distribution of the histogram data for each voxel (step 312). Next, deceit detection unit 250 compares the optical data for several voxels for the examined individual.

Figures 7E, 7F:
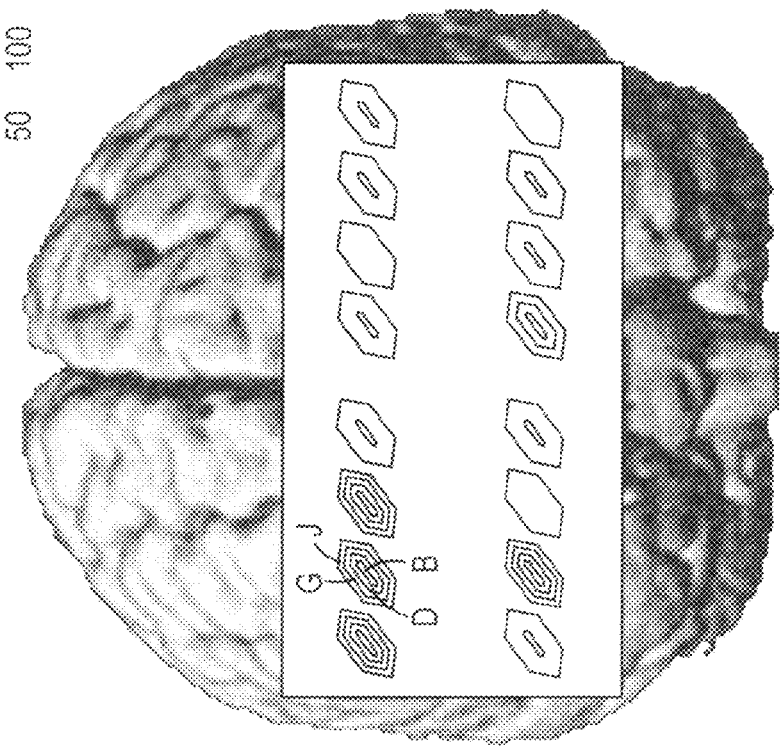
FIGS. 7E and 7F show optical images corresponding to oxygenation changes when the examined individual tells a lie and the truth, respectively
Figure 8:
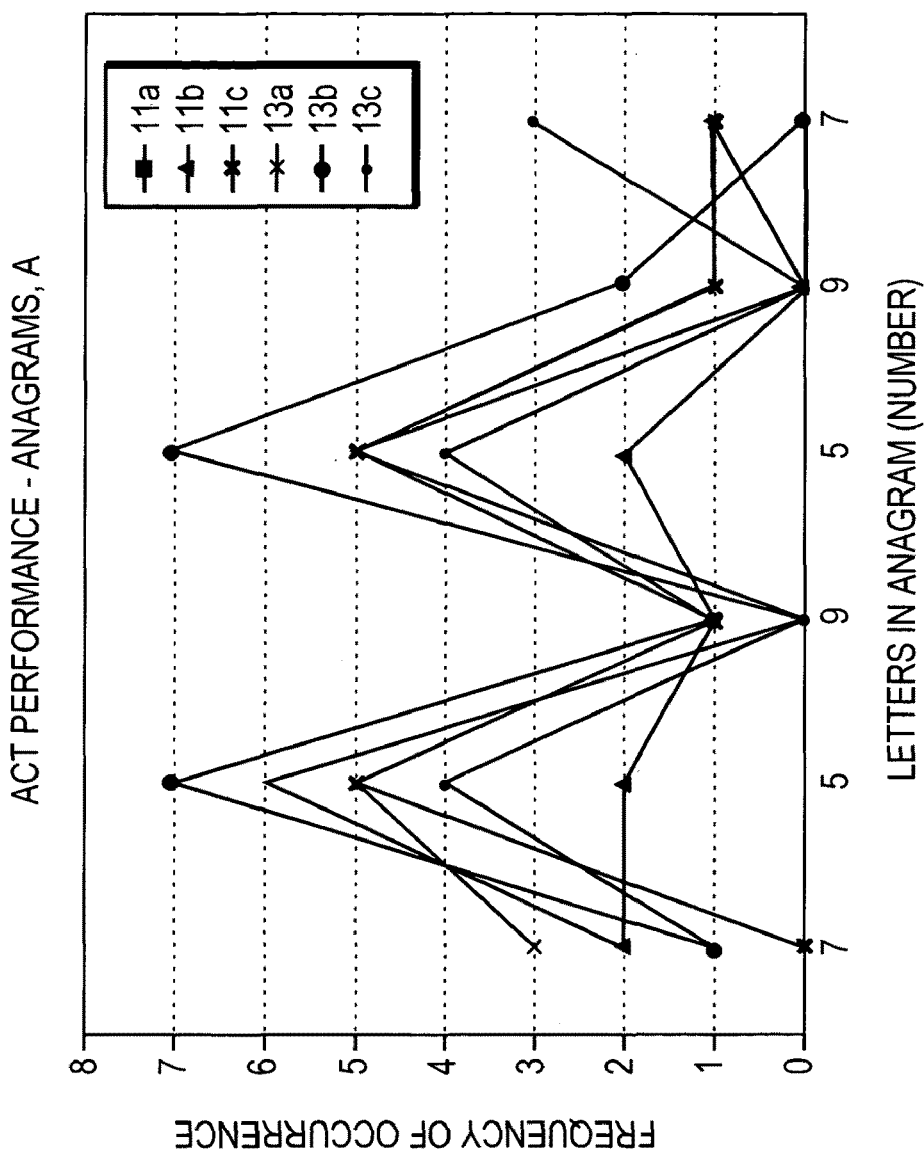
FIG. 8 shows graphically a person's ability to solve anagrams of different length and thus varying difficulty.

Based on the detected intensity of the measured voxels, deceit detection unit 250 determines the "deceit" level corresponding to the optical images. A sample optical image for the examined individual telling a lie is shown in FIG. 7E, and a sample optical image for an individual telling the truth is shown in FIG. 7F. Generally, based on the "background" image of an individual, when an individual is telling the truth the oxygenation images include one or two highly pronounced voxels (FIG. 7F). When the examined individual is lying, the oxygenation images usually provide a large number of active voxels, as shown in FIG. 7E. Deceit detection unit 250 may include a two wavelength or a three wavelength optical system as shown in FIGS. 3, 3A, and 3B.

The "deceit" level may be determined using various criteria. For example, the "deceit" level may be determined by comparing the detected light intensity at each identified voxel. The deceit level may also be determined by measuring a gradient or a distribution of the detected voxels or by correlating the individual images. Alternatively, the deceit level may be determined by receiving input from EEG module 40, MEG module 45, thermography module 50, respiratory module 60, skin conductivity module 70, or blood pressure module 80. Based on the preselected criteria including the comparison for the individual answering various types of questions, deceit detector determines the "deceit" level for further decision.

Based on the "deceit" level determined by detector unit 250, the examined individual may be instructed to proceed to the gate for boarding. Detector unit 250 can print a "security" receipt that is coded to prevent forgery. Detector unit 250 may alternatively "stamp" the individual's airline ticket. To prevent "switching" of the examined individual, detector unit 250 may use fingerprints or a retina scan for identification purposes.

Above a preselected "deceit" level, the deceit detector alarms a security personnel that conducts a manual or x-ray inspection of the individual's luggage, interviews the individual, or takes another action.

The invention claimed is:

1. A method for examining a brain function of a subject, comprising the acts of:
   providing a micro-sensor constructed and arranged to operate at least one light source, and at least one light detector, a battery and a transmitter constructed to transfer data wirelessly;
   introducing optical radiation in the visible to infra-red range from said light source into the brain of a subject and detecting radiation that has migrated in a brain region to a detector pursuant to an activation pulse;
   providing brain stimulation while introducing and detecting said optical radiation;
   wirelessly transmitting data from said at least one light detector to a receiver in synchrony with said activation pulse;
   storing said transmitted data and creating optical data; and
   evaluating said optical data to determine a brain function of the subject.

2. The method of claim 1, wherein said acts of introducing and detecting optical radiation are performed to obtain "rest" optical data at a low level of said brain stimulation, and said acts of introducing and detecting optical radiation are performed to obtain "functional" optical data at a high level of said brain stimulation.

3. The method of claim 1 further including introducing and detecting optical radiation to obtain "background" optical data without said brain stimulation.

4. The method of claim 1, wherein said providing brain stimulation includes providing visual stimulation.

5. The method of claim 4, wherein said providing visual stimulation includes displaying a picture.

6. The method of claim 4, wherein said providing visual stimulation includes displaying a movie.

7. The method of claim 1, wherein said providing brain stimulation includes stimulating cognitive function of the brain.

8. The method of claim 1, wherein said providing brain stimulation includes stimulating memories stored in the brain.

9. The method of claim 1, wherein said providing brain stimulation includes providing auditory stimulation.

10. The method of claim 1, wherein said acts of introducing and detecting optical radiation are performed while performing a mental activity.

11. The method of claim 1, wherein said acts of introducing and detecting optical radiation are performed while performing a physical activity.

12. The method of claim 1, wherein said acts of introducing and detecting optical radiation are performed over an extended period of time.

13. The method of claim 1, wherein said evaluated brain function includes an emotional response.

14. The method of claim 13, wherein said emotional response is a signature of propensity to violent behavior.

15. The method of claim 13, wherein said emotional response is a signature of propensity to antisocial behavior.

16. The method of claim 1, wherein said evaluated brain function includes a cognitive response.

17. The method of claim 1, wherein said evaluated brain function includes an initiated a verbal response.

18. The method of claim 1, wherein said evaluated brain function includes initiated signals to a specific muscle.

19. The method of claim 1, wherein said optical data includes blood volume or blood oxygenation.

20. A system for examining a brain function of a subject, comprising:
    a micro-sensor including at least one light source, at least one light detector, a battery and a transmitter constructed to transfer data wirelessly, said light source being constructed and arranged to introduce optical radiation in the visible to infra-red range transcranially into the brain of a subject and said light detector being constructed and arranged to detect radiation that has migrated in a brain region of the subject pursuant to a activation pulse;
    a stimulation module constructed and arranged to provide brain stimulation while said optical radiation is being introduced and detected;
    a receiver constructed and arranged to "receive and" store said detected radiation in synchrony with said activation pulse, said receiver coupled to electronics arranged and constructed to create optical data; and
    a processor constructed and arranged to evaluate said optical data to determine a brain function of the subject.

21. The system of claim 20, wherein said light source is coupled to a driver, and a timer.

22. The system of claim 20, wherein said light detector is coupled to an amplifier constructed to amplify detector data prior to transmission by said wireless transmitter.

23. The system of claim 20 wherein said wireless optical probe communicates in an ISM band.

24. A system for detecting deceit by a subject, comprising:
a micro-sensor including at least one light source, at least one light detector, a battery and a transmitter constructed to transfer data wirelessly, said light source being constructed and arranged to introduce optical radiation in the visible to infra-red range transcranially into the brain of a subject and said light detector being constructed and arranged to detect radiation that has migrated in a brain region of the brain of the subject pursuant to an activation pulse;
a stimulation module constructed and arranged to provide brain stimulation and to receive a response from said subject while said optical radiation is being introduced and detected;
a receiver constructed and arranged receive transferred data from said transmitter, said receiver coupled to electronics to store said transferred data and to create optical data; and
a computer including a processor programmed to evaluate said optical data to determine whether said response was a knowingly false response.

25. The system of claim 24 further including an EEG module.

26. The system of claim 25, wherein said light detector is coupled to an amplifier constructed to amplify detector data prior to transmission by said wireless transmitter.

27. The system of claim 24 further including an MEG module.

28. The system of claim 27 wherein said wireless optical probe communicates in an ISM band.

29. The system of claim 24 further including a thermography module.

30. The system of claim 24 further including a respiratory module.

31. The system of claim 24 further including a skin conductivity module.

32. The system of claim 24, wherein said light source is coupled to a driver and a timer.

* * * * *